United States Patent [19] — Cole et al.

[11] Patent Number: 5,795,974
[45] Date of Patent: *Aug. 18, 1998

[54] MYCOPLASMA ARTHRITIDIS SUPERANTIGEN

[75] Inventors: Barry C. Cole, Sandy; Curtis L. Atkin, Holladay; Kevin L. Knudtson, Salt Lake City, all of Utah

[73] Assignee: University of Utah Research Foundation, Salt Lake City, Utah

[*] Notice: The term of this patent shall not extend beyond the expiration date of Pat. No. 5,639,869.

[21] Appl. No.: 621,081

[22] Filed: Mar. 22, 1996

Related U.S. Application Data

[63] Continuation-in-part of Ser. No. 165,038, Dec. 10, 1993, Pat. No. 5,639,869.

[51] Int. Cl.$^6$ ................................................ C07N 21/04
[52] U.S. Cl. ............................ 536/23.7; 435/7.2; 435/5
[58] Field of Search ..................... 435/5, 7.2; 536/23.7

[56] References Cited

U.S. PATENT DOCUMENTS 5,639,869  6/1997  Cole et al. ............................ 536/23.7

OTHER PUBLICATIONS

Kevin L. Knudston et al., *Expression of the Mycoplasma Arthritidis Mitogen Gene (mam) In Escherichia coli*, 3 I.O.M. Letters Congress of Intl. Org. Mycoplasmology Jul. 19–26 609–610 (1994) (abstr.)

Barry C. Cole et al., *Immunomodulation In Vivo by the Mycoplasma arthritidis Superantigen, MAM*, 17 Clin. Inf. Dis. S163–S169 (supp. 1, 1993).

C. Gidolf et al., *Antibodies are Capable of Directing Superantigen–mediated T Cell Killing of Chronic B Lymphocytic Leukemia Cells*, 9 Leukemia 1534–42 (1995).

Dohlsten et al., *Antibody–targeted Superantigens are Potent Inducers of Tumor–infiltrating T Lymphocytes in vivo*, 92 Proc. Nat'l. Acad. Sci. USA 9791–9795 (1995).

Dohlsten at al., *Monoclonal Antibody–superantigen Fusion Proteins: Tumor–specific Agents for T–cell–based Tumor Therapy*, 91 Proc. Nat'l.Sci. USA 8945–8949 (1994).

Colin R.A. Hewitt et al., *The Superantigenic Activities of Bacterial Toxins, Molecular Biology of Bacterial Infections* 149–172 (1992).

Janice White et al., *The Vβ–Specific Superantigen Staphylococcal Enterotoxin B: Stimulation of Mature T Cells and Clonal Deletion in Neonatal Mice*, 50 Cell 27–35 (1989).

Barry C. Cole et al., *Stimulation of Mouse Lymphocytes By a Mitogen Derived From Mycoplasma Arthritidis*, 127 The Journal of Immunology 1931–1936 (1981).

Philippa Marrack and John Kappler, *The Staphylococal Enterotoxins and Their Relatives*, 248 Science 705–711 (1990).

Allen D. Sawitzke et al., *Bacterial Superantigens in Disease*, Virulence Mechanisms of Bacterial Pathogens 2nd ed. 145–169 (1995).

(List continued on next page.)

*Primary Examiner*—James C. Housel
*Assistant Examiner*—Ginny Allen Portner
*Attorney, Agent, or Firm*—Thorpe, North & Western, L.L.P.

[57] ABSTRACT

The gene encoding the superantigen *Mycoplasma arthritidis* T-cell mitogen (MAM) was molecularly cloned. The mam gene was modified by site-directed mutagenesis to change UGA codons, which in mycoplasmas are read as tryptophan codons instead of universal stop codons, to UGG codons such that the gene could be expressed in standard expression systems. Recombinant MAM, including extra amino acid residues at the N- and C-termini, were expressed and discovered to be biologically active. Certain amino acid substitutions in active regions of the protein also yield biologically active MAM proteins. A method of diagnosing rheumatoid arthritis using recombinant MAM protein in an ELISA assay is disclosed.

17 Claims, 3 Drawing Sheets

OTHER PUBLICATIONS

Andrew Herman et al., *HLA–DR Alleles Differ in Their Ability to Present Staphylococcal Enterotoxins to T Cells*, 172 J. Exp Med 709–717 (1990).

Paul R. Scholl et al., *Staphylococcal Enterotoxin B and Toxic Shock Syndrome Toxin–1 Bind to Distinct Sites on HLA–DR and HLA–DQ Molecules*, 143 The Journal of Immunology 2583–2588 (1989).

James M. Musser et al., *A Single Clone of Staphylococcus Aureus Causes the Majority of Cases of Ttoxic Shock Syndrome*, 87 Proc. Nat'l. Acad. Sci. USA 225–229 (1990).

Mark A. Tomai et al., *Distinct T–Cell Receptor Vβ Gene Usage by Human T Lymphocytes Stimulated with the Streptococcal Pyrogenic Exotoxins and pep M5 Protein*, 60 Infection and Immunity 701–705 (1992).

Xiaowen He et al., *Selective Induction of Rheumatoid Factors by Superantigens and Human Helper T Cells*, 89 J. Clin. Invest. 673–680 (1992).

Mary K. Crow et al., *Human B Cell Differentiation Induced By Microbial Superantigens: Unselected Peripheral Blood Lymphocytes Secrete Polyclonal Immunoglobulin Response to Mycoplasma Arthritidis Mitogen*, 14 Autoimmunity 23–32 (1992).

Anne C. Avery et al., *Activation of T Cells by Superantigen in Class II–Negative Mice*, 153 The Journal of Immunology 4853–4861 (1994).

Barry C. Cole et al., *Influence of Genes of the Major Histocompatibility Complex on Ulcerative Dermal Necrosis Induced in Mice by Mycoplasma arthritidis*, 85 The Journal of Investigative Dermatology 357–361 (1985).

Barry C. Cole et al., *Toxicity But Not Arthritogenicity of Mycoplasma arthritidis from Mice Associates with the Haplotype Expressed at the Major Histocompatibility Complex*, 41 Infection and Immunity 1010–1015 (1983).

Roberto Baccala et al., *Mycoplasma Arthritidis Mitogen Vβ Engaged in Mice, Rats, and Humans, and Requirement of HLA–DRá for Presentation*, 35 Arthritis and Rheumatism 434–441 (1992).

Barry C. Cole et al., *Immunosuppressive Properties of the Mycoplasma arthritidis T–Cell Mitogen In Vivo: Inhibition of Proliferative Responses to T–Cell Mitogens*, 58 Infection and Immunity 228–236 (1990).

Barry C. Cole and Marie M. Griffiths, *Triggering and Exacerbation of Autoimmune Arthritis by the Mycoplasma Arthritidis Superantigen MAM*, 36 Arthritis and Rheumatism 994–1002 (1993).

Curtis L. Atkin et al., *the Mycoplasma arthritidis Superantigen MAM: Purification and Identification of an Active Peptide*, 62 Infection and Immunity 5367–5374 (1994).

Barry C. Cole et al., *Stimulation of Mouse Lymphocytes by a Mitogen Derived from Mycoplasma Arthritidis IV. Murine T Hybridoma Cells Exhibit Differential Accessory Cell Requirements for Activation by M. arthritidis T Cell Mitogen, Concanavalin A, or Hen Egg–white Lysozyme*, 136 The Journal of Immunology 3572–3578.1986.

Curtis L. Atkin et al., *Stimulation of Mouse Lymphcytes by a Mitogen Derived from Mycoplasma Arthritidis V. A Small Basic Protein from Culture Supernatants Is a Potent T Cell Mitogen*, 137 The Journal of Immunology 1581–1589 (1986).

Steven M. Friedman et al., *A Potential Role for Microbial Superantigens in the Pathogenesis of Systemic Autoimmune Disease*, 34 Arthritis and Rheumatism 468–480 (1991).

Barry C. Cole et al., *Genomic Composition and Allelic Polymorphisms Influence Vβ Usage by the Mycoplasma Arthritidis Superantigen*, 150 The Journal of Immunology 1–9 (1993).

Kotzin, BC et al, Adv. Immunol, vol. 54, p. 99–p.166, 1993.

Friedman, S.M et al. J. Exp. Med., vol. 174(4), pp. 891–900, 1991.

Cole, BC et al, J.of Exp. Med., vol. 183(3), pp. 1105–1110, 1996.

Cole, BC, Current Topics in Microbiol. & Immun., pp. 107–119, vol. 174, 1991.

Swada, T et al, Infect. & Immun., vol. 63(9), pp. 3367–3372, 1995.

Sambrook et , Molecular Cloning, Chapter 15 pp. 15.2–15.113, 1989.

Knudtson, KL et al, IOM Letters, vol. 3, Congress of Intl'l Org. Mycoplasmology, Jul. 19–26, 1994.

Atkin, CL et al, (Reg.), Infect. & Immun., vol. 62(1), pp. 5367–5375, 1994.

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
( A ) LENGTH: 54 amino acids
( B ) TYPE: amino acid
( D ) TOPOLOGY: linear ( i i ) MOLECULE TYPE: protein ( i i i ) HYPOTHETICAL: no ( i v ) ANTI-SENSE: no ( v ) FRAGMENT TYPE: N-terminal fragment ( v i ) ORIGINAL SOURCE:
( A ) ORGANISM: Mycoplasma arthritidis
( B ) STRAIN: PG6
( G ) CELL TYPE: unicellular organism ( i x ) FEATURE:
( A ) NAME/KEY: N-terminal region of mature protein
( B ) LOCATION: 1 to 54
( C ) IDENTIFICATION METHOD: direct sequencing of protein
( D ) OTHER INFORMATION: contains domain that blocks cell proliferation ( x i ) SEQUENCE DESCRIPTION: SEQ ID NO:1:

| Met | Lys | Leu | Arg | Val | Glu | Asn | Pro | Lys | Lys | Ala | Gln | Lys | His | Phe | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gln | Asn | Leu | Asn | Asn | Val | Val | Phe | Thr | Asn | Lys | Glu | Leu | Glu | Asp | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Asn | Leu | Ser | Asn | Lys | Glu | Glu | Thr | Lys | Glu | Val | Leu | Lys | Leu | Phe |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Lys | Leu | Lys | Val | Xaa | Gln |
|-----|-----|-----|-----|-----|-----|
| 50  |     |     |     |     |     |

( 2 ) INFORMATION FOR SEQ ID NO:2:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i i ) HYPOTHETICAL: yes ( i v ) ANTI-SENSE: no ( v i ) ORIGINAL SOURCE:
        ( A ) ORGANISM: Mycoplasma arthritidis
        ( B ) STRAIN: PG6
        ( G ) CELL TYPE: unicellular organism ( x i ) SEQUENCE DESCRIPTION: SEQ ID NO:2:

GAAAAYCCAA AAAAAGCWCA AAAACA                    2 6

( 2 ) INFORMATION FOR SEQ ID NO:3:

( i ) SEQUENCE CHARACTERISTICS:
        ( A ) LENGTH: 1107
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
        ( A ) ORGANISM: Mycoplasma arthritidis
        ( B ) STRAIN: PG6
        ( G ) CELL TYPE: unicellular organism ( x i ) SEQUENCE DESCRIPTION: SEQ ID NO:3:

TTTAACACTT CTTTCGGTTA TTAATAACTT TAAATTCTAA TTAAATTGGT AAAGCGGGTA    60

AACAAAGAAA CTATTTAAAA ATTTATGAAA TTAATATTTA ACTTTATAAA ATAAAATTTC    120

| GCTGTGAAA | ATG | AAA | TTC | TTC | ACA | AAT | TTA | AAA | ATC | ATA | AGG | AAT | AAA | AAA | 171 |
|-----------|-----|-----|-----|-----|-----|-----|-----|-----|-----|-----|-----|-----|-----|-----|-----|
|           | Met | Lys | Phe | Phe | Thr | Asn | Leu | Lys | Ile | Ile | Arg | Asn | Lys | Lys |     |
|           |     |     | -35 |     |     |     |     |     |     | -30 |     |     |     |     |     |

| ATG | AAA | ACA | AAA | AAA | TTA | TTA | ATC | GCA | ACC | GTC | ACT | TTA | GCG | ACT | GGG | 219 |
|-----|-----|-----|-----|-----|-----|-----|-----|-----|-----|-----|-----|-----|-----|-----|-----|-----|
| Met | Lys | Thr | Lys | Lys | Leu | Leu | Ile | Ala | Thr | Val | Thr | Leu | Ala | Thr | Gly |     |
| -25 |     |     |     | -20 |     |     |     |     | -15 |     |     |     |     | -10 |     |     |

| CTT | TTA | GGA | ATT | TTA | CCA | TTA | ACT | AGC | ATG | AAA | CTT | AGA | GTT | GAA | AAT | 267 |
|-----|-----|-----|-----|-----|-----|-----|-----|-----|-----|-----|-----|-----|-----|-----|-----|-----|
| Leu | Leu | Gly | Ile | Leu | Pro | Leu | Thr | Ser | Met | Lys | Leu | Arg | Val | Glu | Asn |     |
|     |     |     |     | -5  |     |     |     |     | 1   |     |     |     | 5   |     |     |     |

| CCT | AAA | AAA | GCT | CAA | AAG | CAT | TTT | GTG | CAA | AAT | TTA | AAT | AAT | GTT | GTA | 315 |
|-----|-----|-----|-----|-----|-----|-----|-----|-----|-----|-----|-----|-----|-----|-----|-----|-----|
| Pro | Lys | Lys | Ala | Gln | Lys | His | Phe | Val | Gln | Asn | Leu | Asn | Asn | Val | Val |     |
|     |     | 10  |     |     |     | 15  |     |     |     | 20  |     |     |     |     |     |     |

| TTT | ACT | AAT | AAA | GAG | CTT | GAA | GAT | ATC | TAC | AAT | TTA | AGT | AAT | AAA | GAA | 363 |

|  | Phe | Thr | Asn | Lys | Glu | Leu | Glu | Asp | Ile | Tyr | Asn | Leu | Ser | Asn | Lys | Glu |  |
|---|---|---|---|---|---|---|---|---|---|---|---|---|---|---|---|---|---|
|  |  | 25 |  |  |  | 30 |  |  |  |  |  | 35 |  |  |  |  |  |

| GAA | ACA | AAA | GAA | GTA | TTA | AAA | TTG | TTT | AAA | TTG | AAG | GTC | AAC | CAA | TTT | 411 |
|---|---|---|---|---|---|---|---|---|---|---|---|---|---|---|---|---|
| Glu | Thr | Lys | Glu | Val | Leu | Lys | Leu | Phe | Lys | Leu | Lys | Val | Asn | Gln | Phe |  |
| 40 |  |  |  |  | 45 |  |  |  |  | 50 |  |  |  |  | 55 |  |

| TAT | AGA | CAT | GCT | TTT | GGT | ATA | GTG | AAT | GAC | TAC | AAT | GGA | CTT | CTT | GAA | 459 |
| Tyr | Arg | His | Ala | Phe | Gly | Ile | Val | Asn | Asp | Tyr | Asn | Gly | Leu | Leu | Glu |  |
|  |  |  |  | 60 |  |  |  |  | 65 |  |  |  |  | 70 |  |  |

| TAC | AAA | GAA | ATT | TTT | AAT | ATG | ATG | TTT | TTA | AAA | TTA | AGC | GTT | GTC | TTT | 507 |
| Tyr | Lys | Glu | Ile | Phe | Asn | Met | Met | Phe | Leu | Lys | Leu | Ser | Val | Val | Phe |  |
|  |  |  | 75 |  |  |  |  | 80 |  |  |  |  | 85 |  |  |  |

| GAC | ACA | CAA | CGT | AAA | GAG | GCA | AAT | AAC | GTC | GAA | CAA | ATC | AAA | AGA | AAT | 555 |
| Asp | Thr | Gln | Arg | Lys | Glu | Ala | Asn | Asn | Val | Glu | Gln | Ile | Lys | Arg | Asn |  |
|  |  | 90 |  |  |  |  | 95 |  |  |  |  | 100 |  |  |  |  |

| ATC | GCT | ATT | TTA | GAT | GAA | ATA | ATG | GCA | AAA | GCA | GAT | AAC | GAT | TTA | TCT | 603 |
| Ile | Ala | Ile | Leu | Asp | Glu | Ile | Met | Ala | Lys | Ala | Asp | Asn | Asp | Leu | Ser |  |
|  | 105 |  |  |  |  | 110 |  |  |  |  | 115 |  |  |  |  |  |

| TAC | TTT | ATA | TCT | CAG | AAT | AAG | AAT | TTT | CAA | GAG | TTA | TGA | GAT | AAA | GCT | 651 |
| Tyr | Phe | Ile | Ser | Gln | Asn | Lys | Asn | Phe | Gln | Glu | Leu | Trp | Asp | Lys | Ala |  |
| 120 |  |  |  |  | 125 |  |  |  |  | 130 |  |  |  |  | 135 |  |

| GTC | AAA | CTA | ACT | AAA | GAA | ATG | AAA | ATA | AAA | CTT | AAA | TTC | CAA | AAA | CTA | 699 |
| Val | Lys | Leu | Thr | Lys | Glu | Met | Lys | Ile | Lys | Leu | Lys | Phe | Gln | Lys | Leu |  |
|  |  |  |  | 140 |  |  |  |  | 145 |  |  |  |  | 150 |  |  |

| GAT | CTT | CGT | GAT | GGT | GAA | GTT | GCA | ATA | AAC | AAA | GTA | AGA | GAA | TTA | TTT | 747 |
| Asp | Leu | Arg | Asp | Gly | Glu | Val | Ala | Ile | Asn | Lys | Val | Arg | Glu | Leu | Phe |  |
|  |  |  | 155 |  |  |  |  | 160 |  |  |  |  | 165 |  |  |  |

| GGC | AGC | GAC | AAA | AAT | GTA | AAA | GAG | CTT | TGA | TGA | TTT | AGA | TCT | CTT | CTA | 795 |
| Gly | Ser | Asp | Lys | Asn | Val | Lys | Glu | Leu | Trp | Trp | Phe | Arg | Ser | Leu | Leu |  |
|  |  | 170 |  |  |  |  | 175 |  |  |  |  | 180 |  |  |  |  |

| GTA | AAA | GGT | GTT | TAC | CTT | ATA | AAA | CGC | TAT | TAC | GAA | GGT | GAT | ATT | GAA | 843 |
| Val | Lys | Gly | Val | Tyr | Leu | Ile | Lys | Arg | Tyr | Tyr | Glu | Gly | Asp | Ile | Glu |  |
|  | 185 |  |  |  |  | 190 |  |  |  |  | 195 |  |  |  |  |  |

| CTT | AAA | ACG | ACA | TCG | GAT | TTT | GCA | AAA | GCT | GTT | TTT | GAA | GAT |  |  | 885 |
| Leu | Lys | Thr | Thr | Ser | Asp | Phe | Ala | Lys | Ala | Val | Phe | Glu | Asp |  |  |  |
| 200 |  |  |  |  | 205 |  |  |  |  | 210 |  |  |  |  |  |  |

| TAATATTAAA | CATATATAAC | AAATTATCCC | CCCAATCTAA | AAGGTTGGGG | GGATTTTAAA | 945 |
|---|---|---|---|---|---|---|
| TAAATTCCTT | GCATCTAGCA | AGGATAAATA | AGATAGAAAT | AAATTGGTTA | GTTAAAAAAT | 1005 |
| GTTTGGTCCG | TTGCAATTAT | GATTTTTTCG | TTTTGTATTG | TAATTGGCAC | TTCGCTATAT | 1065 |
| TCCTTTATTT | TTCCAGAAAT | AATTTCCATA | GCAAGCATGT | TT |  | 1107 |

( 2 ) INFORMATION FOR SEQ ID NO:4:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Mycoplasma arthritidis
        ( B ) STRAIN: PG6
        ( G ) CELL TYPE: unicellular organism ( x i ) SEQUENCE DESCRIPTION: SEQ ID NO:4:

| Met | Lys | Leu | Arg | Val | Glu | Asn | Pro | Lys | Lys | Ala | Gln | Lys | His | Phe | Val |
|---|---|---|---|---|---|---|---|---|---|---|---|---|---|---|---|
| 1 |  |  |  | 5 |  |  |  |  | 10 |  |  |  |  | 15 |  |

| Gln | Asn | Leu | Asn | Asn | Val | Val | Phe | Thr | Asn | Lys | Glu | Leu | Glu | Asp | Ile |
|  |  |  | 20 |  |  |  |  | 25 |  |  |  |  | 30 |  |  |

| Tyr | Asn | Leu | Ser | Asn | Lys | Glu | Glu | Thr | Lys | Glu | Val | Leu | Lys | Leu | Phe |
|  |  | 35 |  |  |  |  | 40 |  |  |  |  | 45 |  |  |  |

```
Lys  Leu  Lys  Val  Asn  Gln  Phe  Tyr  Arg  His  Ala  Phe  Gly  Ile  Val  Asn
     50                  55                      60

Asp  Tyr  Asn  Gly  Leu  Leu  Glu  Tyr  Lys  Glu  Ile  Phe  Asn  Met  Met  Phe
65                       70                      75                           80

Leu  Lys  Leu  Ser  Val  Val  Phe  Asp  Thr  Gln  Arg  Lys  Glu  Ala  Asn  Asn
                    85                       90                           95

Val  Glu  Gln  Ile  Lys  Arg  Asn  Ile  Ala  Ile  Leu  Asp  Glu  Ile  Met  Ala
               100                      105                      110

Lys  Ala  Asp  Asn  Asp  Leu  Ser  Tyr  Phe  Ile  Ser  Gln  Asn  Lys  Asn  Phe
          115                      120                      125

Gln  Glu  Leu  Trp  Asp  Lys  Ala  Val  Lys  Leu  Thr  Lys  Glu  Met  Lys  Ile
     130                      135                 140

Lys  Leu  Lys  Gly  Gln  Lys  Leu  Asp  Leu  Arg  Asp  Gly  Glu  Val  Ala  Ile
145                      150                 155                           160

Asn  Lys  Val  Arg  Glu  Leu  Phe  Gly  Ser  Asp  Lys  Asn  Val  Lys  Glu  Leu
                    165                 170                      175

Trp  Trp  Phe  Arg  Ser  Leu  Leu  Val  Lys  Gly  Val  Tyr  Leu  Ile  Lys  Arg
               180                 185                      190

Tyr  Tyr  Glu  Gly  Asp  Ile  Glu  Leu  Lys  Thr  Thr  Ser  Asp  Phe  Ala  Lys
          195                 200                      205

Ala  Val  Phe  Glu  Asp
          210
```

( 2 ) INFORMATION FOR SEQ ID NO:5:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO:5:

GAAGAGATCT AAACCACCAG AGCTC         25

( 2 ) INFORMATION FOR SEQ ID NO:6:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO:6:

GATAAAGCTG TCAAACTAAC T         21

( 2 ) INFORMATION FOR SEQ ID NO:7:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO:7:

GTTTGACTGC TTTATCCCAT AACTCTTG         28

( 2 ) INFORMATION FOR SEQ ID NO:8:

( i ) SEQUENCE CHARACTERISTICS:
        ( A ) LENGTH: 28
        ( B ) TYPE: nucleic acid
        ( C ) STRANDEDNESS: single ( D ) TOPOLOGY: linear ( x i ) SEQUENCE DESCRIPTION: SEQ ID NO:8:

CAAGAGTTAT GGGATAAAGC TGTCAAAC                                              28

( 2 ) INFORMATION FOR SEQ ID NO:9:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO:9:

TCAGAATTCA TGAAACTTAG AGTTGAAATC TT                                          32

( 2 ) INFORMATION FOR SEQ ID NO:10:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO:10:

AAAAAGCTTG CAAGGAATTT ATTTAAAATC CCCCC                                       35

( 2 ) INFORMATION FOR SEQ ID NO:11:

( i ) SEQUENCE CHARACTERISTICS:
        ( A ) LENGTH: 729
        ( B ) TYPE: nucleic acid
        ( C ) STRANDEDNESS: double
        ( D ) TOPOLOGY: linear ( x i ) SEQUENCE DESCRIPTION: SEQ ID NO:11:

```
TCAGAATTC ATG AAA CTT AGA GTT GAA AAT CCT AAA AAA GCT CAA AAG              48
          Met Lys Leu Arg Val Glu Asn Pro Lys Lys Ala Gln Lys
           1               5                  10

CAT TTT GTG CAA AAT TTA AAT AAT GTT GTA TTT ACT AAT AAA GAG CTT             96
His Phe Val Gln Asn Leu Asn Asn Val Val Phe Thr Asn Lys Glu Leu
 15                  20                  25

GAA GAT ATC TAC AAT TTA AGT AAT AAA GAA GAA ACA AAA GAA GTA TTA            144
Glu Asp Ile Tyr Asn Leu Ser Asn Lys Glu Glu Thr Lys Glu Val Leu
 30                  35                  40                  45

AAA TTG TTT AAA TTG AAG GTC AAC CAA TTT TAT AGA CAT GCT TTT GGT            192
Lys Leu Phe Lys Leu Lys Val Asn Gln Phe Tyr Arg His Ala Phe Gly
                 50                  55                  60

ATA GTG AAT GAC TAC AAT GGA CTT CTT GAA TAC AAA GAA ATT TTT AAT            240
Ile Val Asn Asp Tyr Asn Gly Leu Leu Glu Tyr Lys Glu Ile Phe Asn
                 65                  70                  75

ATG ATG TTT TTA AAA TTA AGC GTT GTC TTT GAC ACA CAA CGT AAA GAG            288
Met Met Phe Leu Lys Leu Ser Val Val Phe Asp Thr Gln Arg Lys Glu
         80                  85                  90

GCA AAT AAC GTC GAA CAA ATC AAA AGA AAT ATC GCT ATT TTA GAT GAA            336
Ala Asn Asn Val Glu Gln Ile Lys Arg Asn Ile Ala Ile Leu Asp Glu
         95                  100                 105

ATA ATG GCA AAA GCA GAT AAC GAT TTA TCT TAC TTT ATA TCT CAG AAT            384
Ile Met Ala Lys Ala Asp Asn Asp Leu Ser Tyr Phe Ile Ser Gln Asn
110                  115                 120                 125

AAG AAT TTT CAA GAG TTA TGG GAT AAA GCT GTC AAA CTA ACT AAA GAA            432
Lys Asn Phe Gln Glu Leu Trp Asp Lys Ala Val Lys Leu Thr Lys Glu
                 130                 135                 140

ATG AAA ATA AAA CTT AAA TTC CAA AAA CTA GAT CTT CGT GAT GGT GAA            480
```

|  |  |  |  |  |  |  |  |  |  |  |  |  |  |  |  |
|---|---|---|---|---|---|---|---|---|---|---|---|---|---|---|---|
| Met | Lys | Ile | Lys | Leu | Lys | Gly | Gln | Lys | Leu | Asp | Leu | Arg | Asp | Gly | Glu |
|  |  |  | 145 |  |  |  |  | 150 |  |  |  |  | 155 |  |  |

```
GTT GCA ATA AAC AAA GTA AGA GAA TTA TTT GGC AGC GAC AAA AAT GTA       528
Val Ala Ile Asn Lys Val Arg Glu Leu Phe Gly Ser Asp Lys Asn Val
        160             165                 170

AAA GAG CTC TGG TGG TTT AGA TCT CTT CTA GTA AAA GGT GTT TAC CTT       576
Lys Glu Leu Trp Trp Phe Arg Ser Leu Leu Val Lys Gly Val Tyr Leu
    175             180                 185

ATA AAA CGC TAT TAC GAA GGT GAT ATT GAA CTT AAA ACG ACA TCG GAT       624
Ile Lys Arg Tyr Tyr Glu Gly Asp Ile Glu Leu Lys Thr Thr Ser Asp
190             195                 200                 205

TTT GCA AAA GCT GTT TTT GAA GAT TAATATTAAA CATATATAAC                 668
Phe Ala Lys Ala Val Phe Glu Asp
                210

AAATTATCCC CCCAATCTAA AAGGTTGGGG GGATTTTAAA                           708

TAAATTCCTT GCAAGCTTTT T    729
```

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

Ile Glu Gly Arg
1

( 2 ) INFORMATION FOR SEQ ID NO:13:

( i ) SEQUENCE CHARACTERISTICS:
        ( A ) LENGTH: 217 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Ile Ser Glu Phe Met Lys Leu Arg Val Glu Asn Pro Lys Lys Ala Gln
1               5                   10                  15

Lys His Phe Val Gln Asn Leu Asn Asn Val Val Phe Thr Asn Lys Glu
                20                  25                  30

Leu Glu Asp Ile Tyr Asn Leu Ser Asn Lys Glu Thr Lys Glu Val
            35                  40                  45

Leu Lys Leu Phe Lys Leu Lys Val Asn Gln Phe Tyr Arg His Ala Phe
    50                  55                  60

Gly Ile Val Asn Asp Tyr Asn Gly Leu Leu Glu Tyr Lys Glu Ile Phe
65                  70                  75                  80

Asn Met Met Phe Leu Lys Leu Ser Val Val Phe Asp Thr Gln Arg Lys
                85                  90                  95

Glu Ala Asn Asn Val Glu Gln Ile Lys Arg Asn Ile Ala Ile Leu Asp
                100                 105                 110

Glu Ile Met Ala Lys Ala Asp Asn Asp Leu Ser Tyr Phe Ile Ser Gln
        115                 120                 125

Asn Lys Asn Phe Gln Glu Leu Trp Asp Lys Ala Val Lys Leu Thr Lys
    130                 135                 140

Glu Met Lys Ile Lys Leu Lys Gly Gln Lys Leu Asp Leu Arg Asp Gly
145                 150                 155                 160
```

|     |     |     |     | Asn<br>165 |     |     | Arg |     | Leu<br>170 | Phe | Gly | Ser | Asp | Lys<br>175 | Asn |
| --- | --- | --- | --- | --- | --- | --- | --- | --- | --- | --- | --- | --- | --- | --- | --- |
| Val | Lys | Glu | Leu<br>180 | Trp | Trp | Phe | Arg | Ser<br>185 | Leu | Leu | Val | Lys | Gly<br>190 | Val | Tyr |
| Leu | Ile | Lys<br>195 | Arg | Tyr | Tyr | Glu | Gly<br>200 | Asp | Ile | Glu | Leu | Lys<br>205 | Thr | Thr | Ser |
| Asp | Phe<br>210 | Ala | Lys | Ala | Val | Phe<br>215 | Glu | Asp |     |     |     |     |     |     |     |

( 2 ) INFORMATION FOR SEQ ID NO:14:

( i ) SEQUENCE CHARACTERISTICS:
        ( A ) LENGTH: 62
        ( B ) TYPE: nucleic acid
        ( C ) STRANDEDNESS: single
        ( D ) TOPOLOGY: linear ( x i ) SEQUENCE DESCRIPTION: SEQ ID NO:14:

ACAGAATTCA TTAAGAGGA GAAATTAACC ATGAAACTTA GAGTTGAAAA 50

TCCTAAAAAA GC 62

( 2 ) INFORMATION FOR SEQ ID NO:15:

( i ) SEQUENCE CHARACTERISTICS:
        ( A ) LENGTH: 48
        ( B ) TYPE: nucleic acid
        ( C ) STRANDEDNESS: single
        ( D ) TOPOLOGY: linear ( x i ) SEQUENCE DESCRIPTION: SEQ ID NO:15:

GTAAGCTTAG TGATGGTGAT GGTGATGATC TTCAAAACA GCTTTTGC 48

( 2 ) INFORMATION FOR SEQ ID NO:16:

( i ) SEQUENCE CHARACTERISTICS:
        ( A ) LENGTH: 219 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| Met<br>1 | Lys | Leu | Arg | Val<br>5 | Glu | Asn | Pro | Lys | Lys<br>10 | Ala | Gln | Lys | His | Phe<br>15 | Val |
| --- | --- | --- | --- | --- | --- | --- | --- | --- | --- | --- | --- | --- | --- | --- | --- |
| Gln | Asn | Leu | Asn<br>20 | Asn | Val | Val | Phe | Thr<br>25 | Asn | Lys | Glu | Leu | Glu<br>30 | Asp | Ile |
| Tyr | Asn | Leu<br>35 | Ser | Asn | Lys | Glu | Glu<br>40 | Thr | Lys | Glu | Val | Leu<br>45 | Lys | Leu | Phe |
| Lys | Leu<br>50 | Lys | Val | Asn | Gln | Phe<br>55 | Tyr | Arg | His | Ala | Phe<br>60 | Gly | Ile | Val | Asn |
| Asp<br>65 | Tyr | Asn | Gly | Leu | Leu<br>70 | Glu | Tyr | Lys | Glu | Ile<br>75 | Phe | Asn | Met | Met | Phe<br>80 |
| Leu | Lys | Leu | Ser | Val<br>85 | Val | Phe | Asp | Thr | Gln<br>90 | Arg | Lys | Glu | Ala | Asn<br>95 | Asn |
| Val | Glu | Gln | Ile<br>100 | Lys | Arg | Asn | Ile | Ala<br>105 | Ile | Leu | Asp | Glu | Ile<br>110 | Met | Ala |
| Lys | Ala | Asp<br>115 | Asn | Asp | Leu | Ser | Tyr<br>120 | Phe | Ile | Ser | Gln | Asn<br>125 | Lys | Asn | Phe |
| Gln | Glu<br>130 | Leu | Trp | Asp | Lys | Ala<br>135 | Val | Lys | Leu | Thr | Lys<br>140 | Glu | Met | Lys | Ile |
| Lys | Leu | Lys | Gly | Gln | Lys | Leu | Asp | Leu | Arg | Asp | Gly | Glu | Val | Ala | Ile |

```
                145                    150                      155                       160
Asn  Lys  Val  Arg  Glu  Leu  Phe  Gly  Ser  Asp  Lys  Asn  Val  Lys  Glu  Leu
                    165                      170                      175

Trp  Trp  Phe  Arg  Ser  Leu  Leu  Val  Lys  Gly  Val  Tyr  Leu  Ile  Lys  Arg
                    180                      185                      190

Tyr  Tyr  Glu  Gly  Asp  Ile  Glu  Leu  Lys  Thr  Thr  Ser  Asp  Phe  Ala  Lys
                    195                      200                      205

Ala  Val  Phe  Glu  Asp  His  His  His  His  His  His
          210                      215
```

( 2 ) INFORMATION FOR SEQ ID NO:17:

( i ) SEQUENCE CHARACTERISTICS:
        ( A ) LENGTH: 62
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
CACACCATGG  GACATCACCA  TCACCATCAC  ATGAAACTTA  GAGTTGAAAA                50

TCCTAAAAAA  GC                                                            62
```

( 2 ) INFORMATION FOR SEQ ID NO:18:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
AGCTAAGCTT  TAATCTTCAA  AAACAGCTTT  TCG                                   33
```

( 2 ) INFORMATION FOR SEQ ID NO:19:

( i ) SEQUENCE CHARACTERISTICS:
        ( A ) LENGTH: 221 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met  Gly  His  His  His  His  His  His  Met  Lys  Leu  Arg  Val  Glu  Asn  Pro
 1                    5                      10                      15

Lys  Lys  Ala  Gln  Lys  His  Phe  Val  Gln  Asn  Leu  Asn  Asn  Val  Val  Phe
                    20                      25                      30

Thr  Asn  Lys  Glu  Leu  Glu  Asp  Ile  Tyr  Asn  Leu  Ser  Asn  Lys  Glu  Glu
                    35                      40                      45

Thr  Lys  Glu  Val  Leu  Lys  Leu  Phe  Lys  Leu  Lys  Val  Asn  Gln  Phe  Tyr
          50                      55                      60

Arg  His  Ala  Phe  Gly  Ile  Val  Asn  Asp  Tyr  Asn  Gly  Leu  Leu  Glu  Tyr
65                        70                      75                        80

Lys  Glu  Ile  Phe  Asn  Met  Met  Phe  Leu  Lys  Leu  Ser  Val  Val  Phe  Asp
                    85                      90                      95

Thr  Gln  Arg  Lys  Glu  Ala  Asn  Asn  Val  Glu  Gln  Ile  Lys  Arg  Asn  Ile
                    100                     105                     110

Ala  Ile  Leu  Asp  Glu  Ile  Met  Ala  Lys  Ala  Asp  Asn  Asp  Leu  Ser  Tyr
                    115                     120                     125

Phe  Ile  Ser  Gln  Asn  Lys  Asn  Phe  Gln  Glu  Leu  Trp  Asp  Lys  Ala  Val
          130                     135                     140
```

| Lys | Leu | Thr | Lys | Glu | Met | Lys | Ile | Lys | Leu | Lys | Gly | Gln | Lys | Leu | Asp |
| 145 | | | | | 150 | | | | | 155 | | | | | 160 |

| Leu | Arg | Asp | Gly | Glu | Val | Ala | Ile | Asn | Lys | Val | Arg | Glu | Leu | Phe | Gly |
| | | | | 165 | | | | | 170 | | | | | 175 | |

| Ser | Asp | Lys | Asn | Val | Lys | Glu | Leu | Trp | Trp | Phe | Arg | Ser | Leu | Leu | Val |
| | | | 180 | | | | | 185 | | | | | 190 | | |

| Lys | Gly | Val | Tyr | Leu | Ile | Lys | Arg | Tyr | Tyr | Glu | Gly | Asp | Ile | Glu | Leu |
| | | 195 | | | | | 200 | | | | | 205 | | | |

| Lys | Thr | Thr | Ser | Asp | Phe | Ala | Lys | Ala | Val | Phe | Glu | Asp |
| | 210 | | | | | 215 | | | | | 220 | |

( 2 ) INFORMATION FOR SEQ ID NO:20:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO:20:

AAAAAGCTTG CAAGGAATTT ATTTAAAATC CCCCC 35

( 2 ) INFORMATION FOR SEQ ID NO:21:

( i ) SEQUENCE CHARACTERISTICS:
        ( A ) LENGTH: 217 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| Ile | Ser | Glu | Phe | Met | Lys | Leu | Arg | Val | Glu | Asn | Pro | Lys | Lys | Ala | Gln |
| 1 | | | | 5 | | | | | 10 | | | | | 15 | |

| Lys | His | Ala | Ala | Ala | Ala | Ala | Ala | Asn | Val | Val | Phe | Thr | Asn | Lys | Glu |
| | | | 20 | | | | | 25 | | | | | 30 | | |

| Leu | Glu | Asp | Ile | Tyr | Asn | Leu | Ser | Asn | Lys | Glu | Glu | Thr | Lys | Glu | Val |
| | | | 35 | | | | | 40 | | | | | 45 | | |

| Leu | Lys | Leu | Phe | Lys | Leu | Lys | Val | Asn | Gln | Phe | Tyr | Arg | His | Ala | Phe |
| | 50 | | | | | 55 | | | | | 60 | | | | |

| Gly | Ile | Val | Asn | Asp | Tyr | Asn | Gly | Leu | Leu | Glu | Tyr | Lys | Glu | Ile | Phe |
| 65 | | | | | 70 | | | | | 75 | | | | | 80 |

| Asn | Met | Met | Phe | Leu | Lys | Leu | Ser | Val | Val | Phe | Asp | Thr | Gln | Arg | Lys |
| | | | | 85 | | | | | 90 | | | | | 95 | |

| Glu | Ala | Asn | Asn | Val | Glu | Gln | Ile | Lys | Arg | Asn | Ile | Ala | Ile | Leu | Asp |
| | | | 100 | | | | | 105 | | | | | 110 | | |

| Glu | Ile | Met | Ala | Lys | Ala | Asp | Asn | Asp | Leu | Ser | Tyr | Phe | Ile | Ser | Gln |
| | | 115 | | | | | 120 | | | | | 125 | | | |

| Asn | Lys | Asn | Phe | Gln | Glu | Leu | Trp | Asp | Lys | Ala | Val | Lys | Leu | Thr | Lys |
| | 130 | | | | | 135 | | | | | 140 | | | | |

| Glu | Met | Lys | Ile | Lys | Leu | Lys | Gly | Gln | Lys | Leu | Asp | Leu | Arg | Asp | Gly |
| 145 | | | | | 150 | | | | | 155 | | | | | 160 |

| Glu | Val | Ala | Ile | Asn | Lys | Val | Arg | Glu | Leu | Phe | Gly | Ser | Asp | Lys | Asn |
| | | | | 165 | | | | | 170 | | | | | 175 | |

| Val | Lys | Glu | Leu | Trp | Trp | Phe | Arg | Ser | Leu | Leu | Val | Lys | Gly | Val | Tyr |
| | | | 180 | | | | | 185 | | | | | 190 | | |

| Leu | Ile | Lys | Arg | Tyr | Tyr | Glu | Gly | Asp | Ile | Glu | Leu | Lys | Thr | Thr | Ser |
| | | 195 | | | | | 200 | | | | | 205 | | | |

-continued

Asp Phe Ala Lys Ala Val Phe Glu Asp
210                         215

(2) INFORMATION FOR SEQ ID NO:22:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO:22:

Ile Ser Glu Phe Met Lys Leu Arg Val Glu Asn Pro Lys Lys Ala Gln
1               5                   10                  15

Lys His Phe Val Gln Asn Leu Asn Ala Ala Ala Ala Ala Ala Lys Glu
                20                  25                  30

Leu Glu Asp Ile Tyr Asn Leu Ser Asn Lys Glu Glu Thr Lys Glu Val
            35                  40                  45

Leu Lys Leu Phe Lys Leu Lys Val Asn Gln Phe Tyr Arg His Ala Phe
    50                  55                  60

Gly Ile Val Asn Asp Tyr Asn Gly Leu Leu Glu Tyr Lys Glu Ile Phe
65                  70                  75                  80

Asn Met Met Phe Leu Lys Leu Ser Val Val Phe Asp Thr Gln Arg Lys
                85                  90                  95

Glu Ala Asn Asn Val Glu Gln Ile Lys Arg Asn Ile Ala Ile Leu Asp
                100                 105                 110

Glu Ile Met Ala Lys Ala Asp Asn Asp Leu Ser Tyr Phe Ile Ser Gln
            115                 120                 125

Asn Lys Asn Phe Gln Glu Leu Trp Asp Lys Ala Val Lys Leu Thr Lys
    130                 135                 140

Glu Met Lys Ile Lys Leu Lys Gly Gln Lys Leu Asp Leu Arg Asp Gly
145                 150                 155                 160

Glu Val Ala Ile Asn Lys Val Arg Glu Leu Phe Gly Ser Asp Lys Asn
                165                 170                 175

Val Lys Glu Leu Trp Trp Phe Arg Ser Leu Leu Val Lys Gly Val Tyr
            180                 185                 190

Leu Ile Lys Arg Tyr Tyr Glu Gly Asp Ile Glu Leu Lys Thr Thr Ser
    195                 200                 205

Asp Phe Ala Lys Ala Val Phe Glu Asp
210                         215

(2) INFORMATION FOR SEQ ID NO:23:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO:23:

Ile Ser Glu Phe Met Lys Leu Arg Val Glu Asn Pro Lys Lys Ala Gln
1               5                   10                  15

Lys His Phe Val Gln Asn Leu Asn Asn Val Val Phe Thr Ala Ala Ala
                20                  25                  30

Ala Ala Ala Ile Tyr Asn Leu Ser Asn Lys Glu Glu Thr Lys Glu Val
            35                  40                  45

Leu Lys Leu Phe Lys Leu Lys Val Asn Gln Phe Tyr Arg His Ala Phe
    50                  55                  60

| | | | | | | | | | | | | | | |
|---|---|---|---|---|---|---|---|---|---|---|---|---|---|---|
|Gly|Ile|Val|Asn|Asp|Tyr|Asn|Gly|Leu|Leu|Glu|Tyr|Lys|Glu|Ile|Phe|
|65| | | | |70| | | |75| | | | |80|

Asn Met Met Phe Leu Lys Leu Ser Val Val Phe Asp Thr Gln Arg Lys
              85                  90                  95

Glu Ala Asn Asn Val Glu Gln Ile Lys Arg Asn Ile Ala Ile Leu Asp
            100                 105                 110

Glu Ile Met Ala Lys Ala Asp Asn Asp Leu Ser Tyr Phe Ile Ser Gln
        115                 120                 125

Asn Lys Asn Phe Gln Glu Leu Trp Asp Lys Ala Val Lys Leu Thr Lys
    130                 135                 140

Glu Met Lys Ile Lys Leu Lys Gly Gln Lys Leu Asp Leu Arg Asp Gly
145                 150                 155                 160

Glu Val Ala Ile Asn Lys Val Arg Glu Leu Phe Gly Ser Asp Lys Asn
            165                 170                 175

Val Lys Glu Leu Trp Trp Phe Arg Ser Leu Leu Val Lys Gly Val Tyr
            180                 185                 190

Leu Ile Lys Arg Tyr Tyr Glu Gly Asp Ile Glu Leu Lys Thr Thr Ser
        195                 200                 205

Asp Phe Ala Lys Ala Val Phe Glu Asp
210                 215

( 2 ) INFORMATION FOR SEQ ID NO:24:

( i ) SEQUENCE CHARACTERISTICS:
        ( A ) LENGTH: 217 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

Ile Ser Glu Phe Met Lys Leu Arg Val Glu Asn Pro Lys Lys Ala Gln
1               5                   10                  15

Lys His Phe Val Gln Asn Leu Asn Asn Val Val Phe Thr Asn Lys Glu
            20                  25                  30

Leu Glu Asp Ile Tyr Asn Leu Ser Asn Lys Glu Glu Thr Lys Glu Val
        35                  40                  45

Leu Lys Leu Phe Lys Leu Lys Val Asn Gln Phe Tyr Arg His Ala Phe
    50                  55                  60

Gly Ile Val Asn Asp Tyr Asn Gly Leu Leu Glu Tyr Lys Glu Ile Phe
65                  70                  75                  80

Asn Met Met Phe Leu Ala Ala Ala Ala Ala Ala Ala Gln Arg Lys
              85                  90                  95

Glu Ala Asn Asn Val Glu Gln Ile Lys Arg Asn Ile Ala Ile Leu Asp
            100                 105                 110

Glu Ile Met Ala Lys Ala Asp Asn Asp Leu Ser Tyr Phe Ile Ser Gln
        115                 120                 125

Asn Lys Asn Phe Gln Glu Leu Trp Asp Lys Ala Val Lys Leu Thr Lys
    130                 135                 140

Glu Met Lys Ile Lys Leu Lys Gly Gln Lys Leu Asp Leu Arg Asp Gly
145                 150                 155                 160

Glu Val Ala Ile Asn Lys Val Arg Glu Leu Phe Gly Ser Asp Lys Asn
            165                 170                 175

Val Lys Glu Leu Trp Trp Phe Arg Ser Leu Leu Val Lys Gly Val Tyr
            180                 185                 190

Leu Ile Lys Arg Tyr Tyr Glu Gly Asp Ile Glu Leu Lys Thr Thr Ser

```
                    195                         200                         205
Asp  Phe  Ala  Lys  Ala  Val  Phe  Glu  Asp
     210                         215
```

( 2 ) INFORMATION FOR SEQ ID NO:25:

( i ) SEQUENCE CHARACTERISTICS:
        ( A ) LENGTH: 217 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Ile  Ser  Glu  Phe  Met  Lys  Leu  Arg  Val  Glu  Asn  Pro  Lys  Lys  Ala  Gln
 1              5                        10                       15

Lys  His  Phe  Val  Gln  Asn  Leu  Asn  Asn  Val  Val  Phe  Thr  Asn  Lys  Glu
               20                        25                       30

Leu  Glu  Asp  Ile  Tyr  Asn  Leu  Ser  Asn  Lys  Glu  Glu  Thr  Lys  Glu  Val
          35                        40                       45

Leu  Lys  Leu  Phe  Lys  Leu  Lys  Val  Asn  Gln  Phe  Tyr  Arg  His  Ala  Phe
     50                        55                       60

Gly  Ile  Val  Asn  Asp  Tyr  Asn  Gly  Leu  Leu  Glu  Tyr  Lys  Glu  Ile  Phe
65                        70                       75                       80

Asn  Met  Met  Phe  Leu  Lys  Val  Ala  Val  Glu  Leu  Asp  Thr  Gln  Arg  Lys
               85                        90                       95

Glu  Ala  Asn  Asn  Val  Glu  Gln  Ile  Lys  Arg  Asn  Ile  Ala  Ile  Leu  Asp
               100                      105                      110

Glu  Ile  Met  Ala  Lys  Ala  Asp  Asn  Asp  Leu  Ser  Tyr  Phe  Ile  Ser  Gln
               115                      120                      125

Asn  Lys  Asn  Phe  Gln  Glu  Leu  Trp  Asp  Lys  Ala  Val  Lys  Leu  Thr  Lys
     130                      135                      140

Glu  Met  Lys  Ile  Lys  Leu  Lys  Gly  Gln  Lys  Leu  Asp  Leu  Arg  Asp  Gly
145                      150                      155                      160

Glu  Val  Ala  Ile  Asn  Lys  Val  Arg  Glu  Leu  Phe  Gly  Ser  Asp  Lys  Asn
               165                      170                      175

Val  Lys  Glu  Leu  Trp  Trp  Phe  Arg  Ser  Leu  Leu  Val  Lys  Gly  Val  Tyr
               180                      185                      190

Leu  Ile  Lys  Arg  Tyr  Tyr  Glu  Gly  Asp  Ile  Glu  Leu  Lys  Thr  Thr  Ser
          195                      200                      205

Asp  Phe  Ala  Lys  Ala  Val  Phe  Glu  Asp
     210                      215
```

( 2 ) INFORMATION FOR SEQ ID NO:26:

( i ) SEQUENCE CHARACTERISTICS:
        ( A ) LENGTH: 217 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Ile  Ser  Glu  Phe  Met  Lys  Leu  Arg  Val  Glu  Asn  Pro  Lys  Lys  Ala  Gln
 1              5                        10                       15

Lys  His  Phe  Val  Gln  Asn  Leu  Asn  Asn  Val  Val  Phe  Thr  Asn  Lys  Glu
               20                        25                       30

Leu  Glu  Asp  Ile  Tyr  Asn  Leu  Ser  Asn  Lys  Glu  Glu  Thr  Lys  Glu  Val
          35                        40                       45
```

-continued

```
Leu  Lys  Leu  Phe  Lys  Leu  Lys  Val  Asn  Gln  Phe  Tyr  Arg  His  Ala  Phe
     50                  55                       60
Gly  Ile  Val  Asn  Asp  Tyr  Asn  Gly  Leu  Leu  Glu  Tyr  Lys  Glu  Ile  Phe
65                       70                       75                       80
Asn  Met  Met  Phe  Leu  Lys  Val  Ala  Val  Glu  Leu  Asp  Thr  Tyr  Pro  Asn
               85                      90                            95
Thr  Ala  Asn  Asn  Val  Glu  Gln  Ile  Lys  Arg  Asn  Ile  Ala  Ile  Leu  Asp
          100                      105                      110
Glu  Ile  Met  Ala  Lys  Ala  Asp  Asn  Asp  Leu  Ser  Tyr  Phe  Ile  Ser  Gln
          115                      120                      125
Asn  Lys  Asn  Phe  Gln  Glu  Leu  Trp  Asp  Lys  Ala  Val  Lys  Leu  Thr  Lys
     130                      135                      140
Glu  Met  Lys  Ile  Lys  Leu  Lys  Gly  Gln  Lys  Leu  Asp  Leu  Arg  Asp  Gly
145                      150                      155                      160
Glu  Val  Ala  Ile  Asn  Lys  Val  Arg  Glu  Leu  Phe  Gly  Ser  Asp  Lys  Asn
                    165                      170                      175
Val  Lys  Glu  Leu  Trp  Trp  Phe  Arg  Ser  Leu  Leu  Val  Lys  Gly  Val  Tyr
               180                      185                      190
Leu  Ile  Lys  Arg  Tyr  Tyr  Glu  Gly  Asp  Ile  Glu  Leu  Lys  Thr  Thr  Ser
          195                      200                      205
Asp  Phe  Ala  Lys  Ala  Val  Phe  Glu  Asp
     210                      215
```

( 2 ) INFORMATION FOR SEQ ID NO:27:

( i ) SEQUENCE CHARACTERISTICS:
  ( A ) LENGTH: 217 amino acids
  ( B ) TYPE: amino acid
  ( D ) TOPOLOGY: linear ( i i ) MOLECULE TYPE: protein ( x i ) SEQUENCE DESCRIPTION: SEQ ID NO:27:

```
Ile  Ser  Glu  Phe  Met  Lys  Leu  Arg  Val  Glu  Asn  Pro  Lys  Lys  Ala  Gln
1                   5                   10                       15
Lys  His  Phe  Val  Gln  Asn  Leu  Asn  Asn  Val  Val  Phe  Thr  Asn  Lys  Glu
               20                      25                       30
Leu  Glu  Asp  Ile  Tyr  Asn  Leu  Ser  Asn  Lys  Glu  Glu  Thr  Lys  Glu  Val
          35                       40                       45
Leu  Lys  Leu  Phe  Lys  Leu  Lys  Val  Asn  Gln  Phe  Tyr  Arg  His  Ala  Phe
     50                  55                       60
Gly  Ile  Val  Asn  Asp  Tyr  Asn  Gly  Leu  Leu  Glu  Tyr  Lys  Glu  Ile  Phe
65                       70                       75                       80
Asn  Met  Met  Phe  Leu  Ala  Leu  Ser  Val  Val  Phe  Asp  Thr  Gln  Arg  Lys
               85                      90                            95
Glu  Ala  Asn  Asn  Val  Glu  Gln  Ile  Lys  Arg  Asn  Ile  Ala  Ile  Leu  Asp
          100                      105                      110
Glu  Ile  Met  Ala  Lys  Ala  Asp  Asn  Asp  Leu  Ser  Tyr  Phe  Ile  Ser  Gln
          115                      120                      125
Asn  Lys  Asn  Phe  Gln  Glu  Leu  Trp  Asp  Lys  Ala  Val  Lys  Leu  Thr  Lys
     130                      135                      140
Glu  Met  Lys  Ile  Lys  Leu  Lys  Gly  Gln  Lys  Leu  Asp  Leu  Arg  Asp  Gly
145                      150                      155                      160
Glu  Val  Ala  Ile  Asn  Lys  Val  Arg  Glu  Leu  Phe  Gly  Ser  Asp  Lys  Asn
                    165                      170                      175
Val  Lys  Glu  Leu  Trp  Trp  Phe  Arg  Ser  Leu  Leu  Val  Lys  Gly  Val  Tyr
               180                      185                      190
```

```
Leu Ile Lys Arg Tyr Tyr Glu Gly Asp Ile Glu Leu Lys Thr Thr Ser
        195                 200                 205

Asp Phe Ala Lys Ala Val Phe Glu Asp
        210                 215
```

( 2 ) INFORMATION FOR SEQ ID NO:28:

( i ) SEQUENCE CHARACTERISTICS:
        ( A ) LENGTH: 217 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Ile Ser Glu Phe Met Lys Leu Arg Val Glu Asn Pro Lys Lys Ala Gln
 1                   5                  10                  15

Lys His Phe Val Gln Asn Leu Asn Asn Val Val Phe Thr Asn Lys Glu
                 20                  25                  30

Leu Glu Asp Ile Tyr Asn Leu Ser Asn Lys Glu Glu Thr Lys Glu Val
             35                  40                  45

Leu Lys Leu Phe Lys Leu Lys Val Asn Gln Phe Tyr Arg His Ala Phe
    50                  55                  60

Gly Ile Val Asn Asp Tyr Asn Gly Leu Leu Glu Tyr Lys Glu Ile Phe
65                  70                  75                  80

Asn Met Met Phe Leu Lys Leu Ser Val Val Phe Asp Thr Ala Arg Lys
                85                  90                  95

Glu Ala Asn Asn Val Glu Gln Ile Lys Arg Asn Ile Ala Ile Leu Asp
               100                 105                 110

Glu Ile Met Ala Lys Ala Asp Asn Asp Leu Ser Tyr Phe Ile Ser Gln
           115                 120                 125

Asn Lys Asn Phe Gln Glu Leu Trp Asp Lys Ala Val Lys Leu Thr Lys
       130                 135                 140

Glu Met Lys Ile Lys Leu Lys Gly Gln Lys Leu Asp Leu Arg Asp Gly
145                 150                 155                 160

Glu Val Ala Ile Asn Lys Val Arg Glu Leu Phe Gly Ser Asp Lys Asn
               165                 170                 175

Val Lys Glu Leu Trp Trp Phe Arg Ser Leu Leu Val Lys Gly Val Tyr
           180                 185                 190

Leu Ile Lys Arg Tyr Tyr Glu Gly Asp Ile Glu Leu Lys Thr Thr Ser
        195                 200                 205

Asp Phe Ala Lys Ala Val Phe Glu Asp
        210                 215
```

( 2 ) INFORMATION FOR SEQ ID NO:29:

( i ) SEQUENCE CHARACTERISTICS:
        ( A ) LENGTH: 217 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Ile Ser Glu Phe Met Lys Leu Arg Val Glu Asn Pro Lys Lys Ala Gln
 1                   5                  10                  15

Lys His Phe Val Gln Asn Leu Asn Asn Val Val Phe Thr Asn Lys Glu
                 20                  25                  30

Leu Glu Asp Ile Tyr Asn Leu Ser Asn Lys Glu Glu Thr Lys Glu Val
```

|  | 35 |  |  |  | 40 |  |  |  | 45 |  |  |  |
|---|---|---|---|---|---|---|---|---|---|---|---|---|
| Leu | Lys | Leu | Phe | Lys | Leu | Lys | Val | Asn | Gln | Phe | Tyr | Arg | His | Ala | Phe |
|  | 50 |  |  |  | 55 |  |  |  |  |  | 60 |  |  |  |  |

| Gly | Ile | Val | Asn | Asp | Tyr | Asn | Gly | Leu | Leu | Glu | Tyr | Lys | Glu | Ile | Phe |
| 65 | | | | | 70 | | | | | 75 | | | | | 80 |

| Asn | Met | Met | Phe | Leu | Lys | Leu | Ser | Val | Val | Phe | Ala | Thr | Gln | Arg | Lys |
| | | | | 85 | | | | | 90 | | | | | 95 | |

| Glu | Ala | Asn | Asn | Val | Glu | Gln | Ile | Lys | Arg | Asn | Ile | Ala | Ile | Leu | Asp |
| | | | 100 | | | | | 105 | | | | | 110 | | |

| Glu | Ile | Met | Ala | Lys | Ala | Asp | Asn | Asp | Leu | Ser | Tyr | Phe | Ile | Ser | Gln |
| | | 115 | | | | | 120 | | | | | 125 | | | |

| Asn | Lys | Asn | Phe | Gln | Glu | Leu | Trp | Asp | Lys | Ala | Val | Lys | Leu | Thr | Lys |
| | 130 | | | | | 135 | | | | | 140 | | | | |

| Glu | Met | Lys | Ile | Lys | Leu | Lys | Gly | Gln | Lys | Leu | Asp | Leu | Arg | Asp | Gly |
| 145 | | | | | 150 | | | | | 155 | | | | | 160 |

| Glu | Val | Ala | Ile | Asn | Lys | Val | Arg | Glu | Leu | Phe | Gly | Ser | Asp | Lys | Asn |
| | | | | 165 | | | | | 170 | | | | | 175 | |

| Val | Lys | Glu | Leu | Trp | Trp | Phe | Arg | Ser | Leu | Leu | Val | Lys | Gly | Val | Tyr |
| | | | 180 | | | | | 185 | | | | | 190 | | |

| Leu | Ile | Lys | Arg | Tyr | Tyr | Glu | Gly | Asp | Ile | Glu | Leu | Lys | Thr | Thr | Ser |
| | | 195 | | | | | 200 | | | | | 205 | | | |

| Asp | Phe | Ala | Lys | Ala | Val | Phe | Glu | Asp |
| | 210 | | | | | 215 | | |

( 2 ) INFORMATION FOR SEQ ID NO:30:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

| Leu | Ser | Val | Val | Phe | Asp | Thr |
| 1 | | | | 5 | | |

( 2 ) INFORMATION FOR SEQ ID NO:31:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

| Val | Ala | Val | Glu | Leu | Asp | Thr |
| 1 | | | | 5 | | |

( 2 ) INFORMATION FOR SEQ ID NO:32:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

| Val | Ala | Val | Glu | Leu | Asp | Thr | Tyr | Pro | Asn | Thr |
| 1 | | | | 5 | | | | | 10 | |

MYCOPLASMA ARTHRITIDIS SUPERANTIGEN

This application is a continuation-in-part of application Ser. No. 08/165,038, filed Dec. 10, 1993 now U.S. Pat. No. 5,639,869.

This invention was made with government support under grants AI12103 and AR02255 awarded by the U.S. Department of Health and Human Services. The government has certain rights in the invention.

BACKGROUND OF THE INVENTION

This invention relates to compositions and methods of use thereof for detecting an autoimmune disease and treating a selected disease. More particularly, the invention relates to recombinant forms of the superantigen, MAM, from *Mycoplasma arthritidis* and methods of using recombinant forms of MAM for detecting rheumatoid arthritis and treating a selected disease.

In autoimmune disease, a breakdown of self-tolerance leads to generation of an immune response against a specific target antigen or antigens. Microbial agents have long been thought to trigger autoimmune diseases by possessing antigenic determinants that are crossreactive with antigens on target organs. More recently, it has been suggested that superantigens derived from bacteria. P. Marrack & J. Kappler, 248 *Science* 705 (1990); B. Fleischer, 10 *Immunol. Today* 262 (1989), mycoplasma, B. Cole & C. Atkin, 12 *Immunol. Today* 271 (1991), or viruses, W. Frankel et al., 349 *Nature* 526 (1991); P. Dyson et al., 349 *Nature* 531 (1991); Y. Choi et al., 350 *Nature* 203 (1991), may initiate autoimmune disease by activating specific anti-self T cell clones, J. White et al., 56 *Cell* 27 (1989); B. Cole et al., 144 *J. Immunol.* 425 (1990), X. Paliard et al., 253 *Science* 325 (1991), or by forming a superantigen bridge that crosslinks helper T ($T_H$) cells with pre-immune B cells, thereby causing polyclonal B cell activation and secretion of autoimmune antibodies. S. Friedman et al., 34 *Arthritis Rheum.* 468 (1991), W. Mourad et al., 170 *J. Exp. Med.* 2011 (1989). In fact, recent studies have shown that MAM can trigger, enhance, and exacerbate experimental autoimmune collagen-induced arthritis (CIA). B. Cole & M. Griffiths, 36 *Arthritis Rheum.* 994 (1993).

Superantigens are potent mitogens that activate T cells by a unique pathway that binds the major histocompatibility complex (MHC) molecules on accessory cell or B lymphocyte surfaces with specific β-chain variable regions ($V_\beta$) of the α/β T cell receptor for antigen (TCR) present on T cells. Thus, a particular superantigen may be recognized by virtually all T cells that utilize a single or small group of TCR $V_\beta$ gene families. Up to 25% of all T lymphocytes may be activated and hence the name "superantigen". While there is some overlap, each superantigen is recognized by its use of a distinct and characteristic set of TCR $V_\beta$ gene families. Further, superantigens bind selectively and with high affinity to class II MHC molecules. In the absence of antigen processing and in a non-MHC-restricted manner, superantigen-class II MHC antigen complexes on the antigen-presenting cell surface trigger the proliferation of T cells expressing the relevant TCR $V_\beta$ gene products. Finally, the in vivo presence of superantigens profoundly alters the T cell repertoire. During the process of negative selection within the thymus, a superantigen clonally eliminates many of the thymocytes with TCR that bear $V_\beta$ gene products that recognize exactly that superantigen. Superantigens include several staphylococcal enterotoxins, streptococcal pyrogenic exotoxins, a fragment of the group A streptococcus M protein, murine self antigens such as the Mls loci gene products (now known to be encoded by murine tumor retroviruses) and an unknown B cell-specific antigen, a product of Yersinia, rabies, and cytomegalovirus (CMV), and *Mycoplasma arthritidis* T cell mitogen (MAM).

Mycoplasmas are the smallest self-replicating prokaryotes and are parasites of humans, birds, insects, plants, and virtually all other higher life forms. Mycoplasmas are the most common cause of naturally-occurring acute and chronic arthritis in many animal species. *M. arthritidis* is a naturally-occurring arthritogen of rodents that causes a chronic, relapsing disease that, histologically, closely resembles human rheumatoid arthritis. MAM was discovered when live organisms and culture supernatants of *M. arthritidis* were shown to induce the proliferation of, and elicit the differentiation of, cytolytic cells in mouse splenocytes. B. Cole et al., 127 *J. Immunol.* 1931 (1981). An insoluble, presumably membrane-bound B-cell mitogen was found to be associated with mycoplasma cells and was stable at 100° C. In contrast, a soluble T-cell mitogen was present in culture supernatants and was heat labile at 56° C. This heat labile T-cell mitogen is MAM. MAM was then shown to be a potent T-cell mitogen and inducer of gamma-interferon (IFN-γ) for both murine and human lymphocytes. B. Cole et al., 128 *J. Immunol.* 2013 (1982); B. Cole & R. Thorpe, 131 *J. Immunol.* 2392 (1983); B. Cole & R. Thorpe, 43 *Infect. Immun.* 302 (1984); T. Moritz et al., 20 *Scand. J. Immunol.* 365 (1984); H. Kirchner et al., 20 *Scand. J. Immunol.* 133 (1984); H. Kirchner et al., 4 *J. Interferon Res.* 389 (1984).

MAM is produced to maximal titer in senescent broth cultures of *M. arthritidis*. Purification is difficult because MAM is produced in small amounts, is heat and acid (pH<7.0) labile, and has great affinity for surfaces and large molecules, especially nucleic acids. Gel filtration of culture supernatants, at an ionic strength of about 0.5M, indicated that MAM has a molecular mass of about 15 kD whereas PAGE suggested the molecule was about 30 kD. C. Atkin et al., 137 *J. Immunol.* 1581 (1986); H. Kirchner et al., 24 *Scand. J. Immunol.* 245 (1986). Although Kirchner et al. claimed partial purification of MAM, their purification steps would have yielded ≦200-fold purification in the best of hands. Since their mitogenic assay was merely qualitative, they were unable to show yield or specific activity (mitogenicity per unit protein). J. Homfeld et al., 7 *Autoimmunity* 317 (1990), have also described partial purification of MAM. Guided by quantitative assay results for MAM, C. Atkin et al., 137 *J. Immunol.* 1581 (1986), achieved hundreds- to thousands-fold, but still imcomplete, purification of MAM. Active fractions from gel filtration corresponded to the elution volumes of 15–20 kDa standards, although it is now clear that the 15–20 kDa molecular weight then estimated for MAM was anomalous due to MAM-resin binding. Active fractions corresponding to mobilities of about 30 kDa standards were recovered from SDS-PAGE gels, but no stainable band of MAM protein was identified. As MAM from SDS-PAGE was in vanishing amounts, and MAM from chromatography was still very impure, no amino acid sequence was obtained.

U.S. patent application Ser. No. 08/165,038 describes a method for purifying MAM approximately one million-fold to homogeneity in reasonable (about 25%) yield. Still, the miniscule amount of final product (about 3–10 μg per liter of culture) and high expense (about $100,000 per milligram in 1995 dollars) of such homogeneous MAM suggest that improved means of production are needed.

One of the major activities of MAM is its ability to cause a proliferation of lymphocytes from certain strains of mice, but not of others. Lymphocytes from BALB/c and C3H mice are readily activated whereas those of C57BL/10 mice fail to undergo proliferation in response to exposure to MAM. This negative or weak response of C57BL/10 mice enabled mapping one of the genes which control MAM reactivity to the I-E region of the murine H-2 MHC. Dependence upon MHC-bearing accessory cells for MAM-induced T-cell proliferation was consistent with this conclusion. This specificity for I-E bearing cells suggested that the I-E molecule might be the binding site for MAM. The fact that only splenocytes from I-E-bearing mouse strains could remove MAM activity from solution and liposomes with incorporated I-E, but not with I-A, molecules could present MAM to T cells supported this hypothesis. There is substantial evidence that the conserved $\alpha$ chain of the I-E molecule, or a combinatorial determinant between $E_\alpha$ and other $\beta$ chains, bears the MAM receptor. Evidence of this includes ATFR5 mice which lack $E_\beta$ respond to MAM through combinatorial $E_\alpha A_\beta$ molecules, antibodies to a monoclonal antibody specific for $E_\alpha$ totally block MAM-induced proliferation, $E_\alpha$ transgenic mice on a C57BL/10 background present MAM, and transfected fibroblasts expressing $E_\alpha E_\beta$ or $E_\alpha A_\beta$ present MAM, whereas fibroblasts expressing $A_\alpha A_\beta$ do not. B. Cole et al., 127 *J. Immunol.* 1931 (1981); B. Cole et al., 128 *J. Immunol.* 2013 (1982); B. Cole et al., 129 *J. Immunol.* 1352 (1982); B. Cole et al., 136 *J. Immunol.* 3572 (1986); M. Bekoff et al., 139 *J. Immunol.* 3189 (1987); M. Matthes et al., 18 *Eur. J. Immunol.* 1733 (1988); B. Cole et al., 144 *J. Immunol.* 420 (1990).

MAM, like other superantigens, is recognized by $V_\beta$ chain segments of the $\alpha/\beta$ TCR. This was demonstrated in progeny of test-crosses between RIIIS mice, which have massive deletions in their $V_\beta$ $\alpha/\beta$ T-cell repertoire, with (RIIIS× B10.RIII)F1hybrids. B10.RIII mice contain most known $V_\beta$ genes. Reactivity of lymphocytes with MAM cosegregated with expression of $V_\beta 8$-bearing cells. Thus, at least the $V_\beta 8$ TCR gene family was involved in recognition of MAM. In other experiments, clonal expansion of MAM-reactive BALB/c cells in vitro showed the activated cells expressed $V_\beta 8.1$, $V_\beta 8.2$, $V_\beta 8.3$, and $V_\beta 6$. MAM expansion of C57BR lymphocytes, which lack the $V_\beta 8$ genes, resulted in strong expression of $V_\beta 6$ in the activated population. Similarly, it has been shown that MAM can use TCRs expressing $V_\beta 5.1$. These specificities of MAM for certain TCR genes was reported in B. Cole et al., 144 *J. Immunol.* 425 (1990); L. Baccala et al., 35 *Arthritis Rheum.* 434 (1992). In rats, MAM-reactive $V_\beta$ are homologous to the MAM-reactive $V_\beta$ of mice, with one exception. Engagement of rat $V_\beta 5.1$, $V_\beta 6$, $V_\beta 8.1$, and $V_\beta 8.2$, but not $V_\beta 8.3$ were observed. In humans, the engaged $V_\beta$ included primarily $V_\beta 19.1$ (alternatively termed $V_\beta 17.1$) and, to a lesser extent, $V_\beta 3.1$, $V_\beta 11.1$, $V_\beta 12.1$, and $V_\beta 13.1$. R. Baccala et al., 35 *Arthritis Rheum.* 434 (1992). More recent experiments have shown that both genomic composition and allelic polymorphisms at the $V_\beta$ chain segment of the TCR exert profound effects upon the pattern of $V_\beta$ that are used by MAM. Thus, in $V_\beta^b$ haplotype mice, without genomic deletions of $V_\beta$ genes, $V_\beta 5.1$, $6$, $8.1$, $8.2$, and $8.3$ engage MAM. In $V_\beta^a$ mice, with deletions in $V_\beta 5.1$ to $5.3$, $8.1$ to $8.3$, $9$, $11$, $12$, and $13$, there was significant expansion of $V_\beta 6$-expressing cells and lesser expansions of $V_\beta 1$-, $7$-, and $16$-expressing cells. In $V_\beta^c$ mice, with deletions of the same $V_\beta$ genes deleted in $V_\beta^a$ and additional deletions in $V_\beta 6$, $15$, and $17$, there was a dominant expansion of $V_\beta 7$ and $V_\beta 1$, and a slight expansion of $V_\beta 3.1$-expressing cells. B. Cole et al., 150 *J. Immunol.* 3291 (1993). Usage of $V_{\beta 2}$ 8 gene products is fairly common among other microbial superantigens, however $V_\beta 6$ is only used by MAM and the Mls $1^a$ antigen now known to be a murine retroviral superantigen.

MAM can also activate human peripheral blood lymphocytes; this reaction too is dependent upon MHC molecules. The human MHC HLA-DR molecule, the equivalent of the murine H2 I-E molecule, appears to possess the MAM binding site. Evidence of this includes inhibition of T-cell proliferation by anti-HLA-DR antibodies, production of IFN-$\gamma$ and induction of cytolytic cells in response to MAM, and presentation of MAM to human T-cells by cells transfected with I-E and the inhibition of the response by anti-I-E monoclonal antibodies. MAM can produce proliferation of human T-cells regardless of whether the cells express CD4 or CD8 molecules. TCR $\alpha/\beta$-negative, $\gamma/\delta$ -positive cells also respond to MAM in the presence of appropriate accessory cells. R. Daynes et al., 129 *J. Immunol.* 936 (1982); B. Cole & R. Thorpe, 131 *J. Immunol.* 2392 (1983); M. Matthes et al., 18 *Eur. J. Immunol.* 1733 (1988); R. Baccala et al., 35 *Arthritis Rheum.* 434 (1992). The human $V_\beta$ chains that interact with MAM are those that show the greatest degree of sequence homology with their MAM-reactive murine counterparts. N. Bhardwaj et al., 62 *Infect. Immun.* 135 (1994); B. C. Cole & A. Sawitzke, Mechanisms and Models in Rheumatoid Arthritis 46 (1995).

The response of human cells to MAM has always been found to be weaker than that of mouse cells and weaker than to lectin mitogens. In a direct comparison, human cells responded better to staphylococcal superantigens than to MAM, and mouse cells responded better to MAM. B. Fleischer et al., 146 *J. Immunol.* 11 (1991). This difference seems to issue from differences in the MHC/superantigen interaction since lymphocytes from transgenic mice expressing human MHC molecules respond better to staphylococcal superantigens than to MAM.

The apparent ability of individual superantigen molecules to interact simultaneously with MHC molecules on accessory cells and B cells, as well as with $V_\beta$ TCRs on T-cells, raises the possibility that superantigens might be able to initiate a B-$T_H$ cell collaboration resulting in polyclonal B cell activation. Peripheral blood lymphocytes from normal individuals or rheumatoid arthritis patients secreted significantly higher levels of IgG when co-cultured in vitro with MAM and pokeweed mitogen. Further, purified B cell cultures or B cells incubated with MAM-reactive $T_H$ cells failed to secrete significant levels of IgM. However, when B cells were briefly exposed to MAM or when MAM was added to B-$T_H$ cell mixtures, high levels of IgM were produced. This is important because abnormal B-$T_H$ cell interactions mimic the interaction seen in graft versus host disease that has been used as a model of systemic lupus erythematosus (SLE). In SLE, abnormal B cell reactivity results in production of a wide range of autoantibodies. P. Emery et al., 12 *J. Rheumatol.* 217 (1985); J. Tumang et al., 171 *J. Exp. Med.* 2153 (1990); S. Friedman et al., 34 *Arthritis Rheum.* 468 (1991).

*M. arthritidis* also causes a severe suppurative arthritis in rats which can also be associated with uveitis, C. Thirkill & D. Gregerson, 36 *Infect. Immun.* 775 (1982), conjunctivitis, urethritis, lethargy, and paralysis, J. Ward & R. Jones, 5 *Arthritis Rheum.* 163 (1962). MAM can activate rat lymphocytes. B. Cole et al., 36 *Infect. Immun.* 662 (1982). Splenic cells from inbred rat strains August, Buffalo, DA, Lewis, Wistar Furth, and (LEW×BN)F1 all responded well to MAM, but BN and MAXX rats responded very weakly or not at all. Genetic analysis showed that non-RT1 genes control responsiveness to MAM. Both responder and nonresponder splenic cells could bind MAM. These results contrast with the results obtained with non-responder mouse strains, wherein the cells failed to bind MAM due to the absence of the $E_\alpha$ chain of the I-E molecule. B. Cole et al., 129 *J. Immunol.*1352 (1982); B. Cole et al., 136 *J. Immunol.* 2364 (1986).

Interestingly, the genetics of MAM-induced activation of rat lymphocytes resembles that of susceptibility to two experimentally-induced autoimmune diseases, experimental allergic encephalomyelitis (EAE) and collagen-induced arthritis (CIA). Thus, (LEW×BN)F1 rats are susceptible to both EAE and CIA, and responsiveness to MAM is a dominant trait, whereas (DA×BN)F1 rats are resistant to both EAE and CIA, and responsiveness to MAM is recessive. In both EAE and CIA of mice, T-cells expressing $V_\beta 8$ chains of the TCR are involved in disease pathogenesis. Since rat and mouse $V_\beta$ TCRs are quite similar, it is not surprising that MAM also activates rat $V_\beta 8$-bearing T-cells. L. Baccala et al., 35 *Arthritis Rheum.* 434 (1992).

Importantly, this similarity between the genetic predisposition to CIA and lymphocyte reactivity to MAM is now known to be due to involvement of similar $V_\beta$ chain segments of the TCR on T cell surfaces. Thus, T cells bearing $V_\beta 6$, $V_\beta 7$, and $V_\beta 8$ participate in CIA. T. Haqqi et al., 89 *Proc. Nat'l Acad. Sci USA* 1253 (1992). These same $V_\beta$ TCRs are also activated by MAM. B. Cole et al., 150 *J. Immunol.* 3291 (1993), thus presenting a mechanism whereby superantigens might activate autoimmune disease. In fact, recent studies, B. Cole & M. Griffiths, 36 *Arthritis Rheum.* 944 (1993), have demonstrated that the intravenous injection of MAM (1) into mice suboptimally immunized with collagen causes a triggering of arthritis, (2) into mice convalescing from CIA results in a flare of disease activity, and (3) into mice just after injection of collagen causes an acceleration of the development of arthritis.

MAM is also thought to play a role in the pathogenicity of *M. arthritidis* by causing immunosuppression of the host. *M. arthritidis* is frequently harbored in the respiratory tract of apparently healthy mice and rats. Its presence may be undetectable without extensive culturing since an antibody response may not be present. M. Davidson et al., 8 *Curr. Microb.* 205 (1983). Even in experimentally-injected mice and rats, where complement-fixing antibodies are rapidly produced, the immune response to *M. arthritidis* is defective. Neutralizing or growth-inhibiting antibodies, which play a major role in the control of mycoplasma infections, are not produced against *M. arthritidis* in rodents. Opsonizing antibodies are likewise not produced. Probably for these reasons, mycoplasmemia persists for up to 3 weeks in the peripheral circulation of intravenously-injected animals. B. Cole et al., 98 *J. Bacteriol.* 930 (1969); B. Cole & J. Ward, 7 *Infect. Immun.* 691 (1973); B. Cole & J. Ward, 8 *Infect. Immun.* 199 (1973).

MAM may be responsible for depressed host defenses. Mycoplasmas are cleared faster from the peripheral circulation of mouse strains which lack functional I-E molecules than from strains possessing I-E. B. Cole et al., 41 *Infect. Immun.* 1010 (1983). Lymphocytes taken from I-E-bearing mice injected intravenously with MAM exhibit an impaired ability to proliferate in response to MAM, and, to a lesser extent, to lectin mitogens. B. Cole & D. Wells, 58 *Infect. Immun.* 228 (1990). MAM also appears to suppress other T-cell functions, such as contact sensitivity to dinitrofluorobenzene (DNFB) and can prolong skin grafts across H-2 and non-H-2 barriers. In contrast, MAM appears not to have any consistent suppressive effect in vivo on B-cell functions, but, instead, enhances B-cell activity.

MAM also appears at least partially responsible for reactions involving toxicity and necrosis in experimentally-injected mice. One of the earliest symptoms following intravenous injection of large numbers of *M. arthritidis* is a toxic shock syndrome that is analogous to the human condition caused by a staphylococcal superantigen. Symptoms include lethargy, ruffled fur, conjunctivitis, fecal impaction, and death in some individuals. These effects were H-2 restricted in that animals with MAM-reactive lymphocytes were susceptible, whereas animals with MAM-nonreactive lymphocytes were resistant. In part, this reaction may be due to liberation of lymphokines and other inflammatory molecules mediated by MAM-induced activation of lymphocytes and macrophages since large doses of highly purified MAM yielded a similar toxic syndrome, but of much lesser duration and severity. B. Cole et al., 41 *Infect. Immun.* 1010 (1983); B. Cole & D. Wells, 58 *Infect. Immun.* 228 (1990).

MAM also appears to play a role in dermal necrosis induced by subcutaneous injection of *M. arthritidis* in susceptible animals. Susceptible mice possess functional I-E, whereas mice lacking functional I-E developed a suppurative abscess but without dermal damage. B. Cole et al., 85 *J. Invest. Dermatol.* 357 (1985).

OBJECTS AND SUMMARY OF THE INVENTION

An object of the present invention is to provide a recombinant form of MAM that is biologically active.

Another object of the invention is to provide a cost-effective method of purifying relatively large quantities of MAM.

A further object of the invention is to provide a diagnostic test for rheumatoid arthritis using recombinant MAM as a reagent.

Yet another object of the invention is to provide a composition and method for immunizing a warm-blooded animal against rheumatoid arthritis.

These and other objects may be accomplished by providing a recombinant MAM protein that exhibits superantigen activity having an amino acid sequence selected from the group consisting of SEQ ID NO:13, SEQ ID NO:16, SEQ ID NO:19, SEQ ID NO:21, SEQ ID NO:27, SEQ ID NO:28, and SEQ ID NO:29. Another embodiment of a recombinant MAM having superantigen activity is represented by the formula MBP-S-X-rMAM, wherein MBP is the maltose binding protein, S is a spacer, X is a factor Xa protease recognition sequence, and rMAM is a member selected from the group consisting of SEQ ID NO:13, SEQ ID NO:21; SEQ ID NO:27, SEQ ID NO:28, and SEQ ID NO:29. Preferably, rMAM is SEQ ID NO:13 and S comprises 10 asparagine residues. Still another embodiment of a recombinant MAM having superantigen activity comprises an amino acid sequence comprising SEQ ID NO:4 and at least one additional amino acid residue at a terminus thereof.

A polynucleotide comprising a gene encoding a MAM protein that exhibits superantigen activity is also disclosed, wherein the gene is capable of being expressed in an expression system that utilizes a UGA universal stop codon for translation termination. The polynucleotide has a nucleotide sequence selected from the group consisting of SEQ ID NO:11 and sequences substantially homologous therewith. Preferably, the gene has the nucleotide sequence of SEQ ID NO:11. A host cell containing the polynucleotide and capable of expressing a recombinant MAM protein is also described.

A method of detecting rheumatoid arthritis in an individual comprises the steps of:

(a) providing a recombinant MAM protein;
(b) obtaining a sample of serum from the individual;
(c) contacting the recombinant MAM protein with the serum sample such that a complex of an antibody in the serum forms with the recombinant MAM protein; and
(d) detecting the complex as a measure of the antibodies against the recombinant MAM protein in the serum.

Preferably, the recombinant MAM protein has an amino acid sequence selected from the group consisting of SEQ ID NO:13, SEQ ID NO:16, SEQ ID NO:19, SEQ ID NO:21, SEQ ID NO:27, SEQ ID NO:28, and SEQ ID NO:29. The recombinant MAM protein can also be represented by the formula MBP-S-X-rMAM, wherein MBP is the maltose binding protein, S is a spacer, X is a factor Xa protease recognition sequence, and rMAM is a member selected from the group consisting of SEQ ID NO:13, SEQ ID NO:21; SEQ ID NO:27, SEQ ID NO:28, and SEQ ID NO:29. Preferably rMAM is SEQ ID NO:13 and S comprises 10 asparagine residues. The recombinant MAM protein can also comprise an amino acid sequence comprising SEQ ID NO:4 and at least one additional amino acid residue at a terminus thereof.

A method of immunizing a warm-blooded animal against rheumatoid arthritis comprises:
(a) providing a recombinant protein that immunoreacts with anti-MAM antibodies but lacks MAM superantigen activity; and
(b) administering an effective amount of the recombinant protein to the warm-blooded animal such that an immune reaction against said recombinant protein is developed. The recombinant protein preferably has an amino acid sequence selected from the group consisting of SEQ ID NO:22, SEQ ID NO:23, SEQ ID NO:24, SEQ ID NO:25, and SEQ ID NO:26.

A recombinant protein that is recognized by anti-MAM antibodies but lacks MAM superantigen activity for use in immunizing a warm-blooded animal against rheumatoid arthritis is also disclosed. The recombinant protein preferably has an amino acid sequence selected from the group consisting of SEQ ID NO:22, SEQ ID NO:23, SEQ ID NO:24, SEQ ID NO:25, and SEQ ID NO:26.

DETAILED DESCRIPTION OF THE INVENTION

Figure 1:
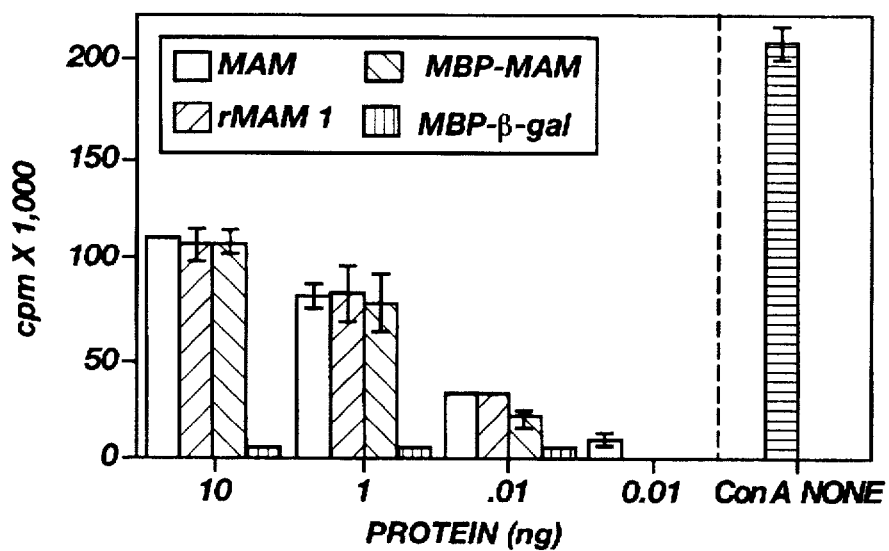
FIG. 1 shows a graphic representation of lymphocyte proliferation by native MAM (MAM), a recombinant MAM (rMAM; SEQ ID NO:13), and maltose-binding-protein-MAM fusion protein (MBP-rMAM) as compared to an MBP-β-galactosidase fusion protein (MBP-β-gal) and concanavalin A (Con A) controls.

Before the present compositions and methods of use thereof for detecting and treating diseases are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition comprising "a MAM protein" includes a mixture of two or more of such MAM proteins.

In describing and claiming the present invention, the following terminology will be used in accordance with the definitions set out below.

As used herein, "expression system" means a host containing a vehicle, such as a plasmid or other DNA sequence that is able to replicate autonomously in such host and is characterized by one or a small number of endonuclease recognition sites at which such DNA sequences may be cut in a determinable fashion without loss of an essential biological function of the vehicle and into which DNA may be spliced to bring about its replication and cloning, such that a gene encoded by the DNA spliced into the vehicle can be expressed. The cloned gene is usually placed under the control of certain control sequences, such as promoter sequences. Expression control sequences will vary depending on whether the vehicle is designed to express the cloned gene in a procaryotic or eucaryotic host and may additionally contain transcription elements, termination sequences, tissue-specificity elements, and/or translational initiation and termination sites.

As used herein, "substantially homologous" refers to a polynucleotide encoding a recombinant MAM protein having superantigen activity wherein the nucleotide sequence of the polynucleotide differs from SEQ ID NO:11 without altering the amino acid sequence of the encoded protein due to the degeneracy of the genetic code. "Substantially homologous" is also intended to include a polynucleotide encoding a recombinant MAM protein that differs from the canonical amino acid sequence of SEQ ID NO:4 but maintains superantigen activity. Such MAM variants include SEQ ID NO:13, SEQ ID NO:16, SEQ ID NO:19, SEQ ID NO:21, SEQ ID NO:27, SEQ ID NO:28, SEQ ID NO:29, and the MBP-MAM fusion protein represented by the formula MBP-S-X-rMAM (described in detail below), and the like. Thus, such MAM variants can include additional amino acid residues at the N- and/or C-terminus as well as certain internal substitutions, deletions, and/or insertions as long as superantigen activity is preserved.

As used herein, "recombinant" refers to a protein expressed in an expression system.

As used herein, "maltose binding protein" or "MBP" means the approximately 45 kDa protein encoded by the E. coli malE gene.

As used herein, "MBP-MAM fusion protein" means a fusion protein produced by cloning a mam gene into a pMAL vector (New England Biolabs, Beverly, Mass.) and expressing a resulting malE-mam gene fusion. An MBP-MAM fusion protein can be represented by the formula MBP-S-X-rMAM, wherein MBP is the maltose binding protein, S is a spacer, X is a factor Xa protease digestion site, and rMAM is a recombinant MAM protein, described in more detail below.

As used herein, "warm-blooded animal" in an animal, including humans, that is susceptible to contracting rheumatoid arthritis.

As used herein, "effective amount" means an amount of a recombinant MAM protein that is nontoxic but sufficient to provide the selected immune response at a reasonable benefit/risk ratio attending any medical treatment. Such an effective amount can be determined by a person of ordinary skill in the art without undue experimentation according to the guidelines presented herein and what is well known in the art.

Construction and Expression of a Recombinant MAM Protein

MAM protein was purified to homogeneity according to the method described in U.S. patent application Ser. No. 08/165,038, which is hereby incorporated by reference. The amino acid sequence of the N-terminal region of homogeneously purified MAM was determined by a pulsed liquid phase method with a BioBreen-treated fiber glass filter sample support based on the Edman degradation method. P. Edman & G. Begg, 1 *Eur. J. Bioch.* 80 (1967); T. Hugli, *Techniques in Protein Chemistry* (1989); P. Matsudaira, *A Practical Guide to Protein and Peptide Purification for Microsequencing* (1989). The machine used was an Applied Biosystems, Inc. (ABI, Foster City, Calif.) Model 477A Protein Sequencer. Using this procedure the sequence of the N-terminal region of mature MAM protein was obtained, which is identified herein as SEQ ID NO:1.

A genomic library of *M. arthritidis* PG-6 was prepared according to standard methods in the EMBL3 phage vector. *M. arthritidis* genomic DNA was partially digested with the restriction endonuclease SalI and then ligated into SalI-digested EMBL3 vector DNA. The resulting library of clones was screened for the MAM gene by Southern hybridization (E. Southern, 98 *J. Mol. Biol.* 503(1975); J. Sambrook et al., *Molecular Cloning* §§ 9.31–9.59 (2d ed., 1989)) with the 5'-hu 32P-phosphorylated synthetic degenerate oligodeoxynucleotide

GAAAAYCCAA AAAAAGCWCA AAAACA (SEQ ID NO:2)

that was designed by reverse translation (according to the codon usage table of Muto, 23 *Israel J. Med. Sci.* 334 (1987), for *Mycoplasma capricolium*), to match as closely as possible the actual coding sequence for amino acids 6–14 of SEQ ID:NO:1. This and other oligodeoxynucleotides were synthesized using an ABI Model 380B DNA Synthesizer with proprietary phosphoramidite chemistry.

Four positive recombinant clones were selected for further characterization, clones 1246, 1410, 1722, and 1903. Southern analysis of these four indicated that a 4 kb HindIII fragment, a 3 kb BamHI fragment, and a 1.6 kb Sau3AI fragment probably each contained the entire MAM gene. These restriction fragments were subcloned into $pBSSK^+$ (Stragene) and pTZ18R (Pharmacia) vectors as follows. Clone pBSMAM-1410-Sau3AI is a subclone of the 1.6 kb Sau3AI fragment of clone 1410 in $pBSSK11^+$. Clones pTZMAM-1722-He and pTZMAM-1722-Hn are subclones, in opposite orientations, of the 4 kb HindIII fragment of clone 1722 in pTZ18R. Nucleotide sequencing of these subclones with the Sanger dideoxynucleotide chain termination method, F. Sanger et al., 74 *Proc. Nat'l Acad. Sci. USA* 5463 (1977), yielded a sequence of the entire MAM gene, SEQ ID NO:3.

The sequenced MAM gene contains a region that, when translated, gives an amino acid sequence identical to that determined by direct amino acid sequencing (amino acids 1–54). This N-terminal region of the mature MAM protein is preceded by a 39 amino acid residue signal peptide or pre-peptide. Mature MAM (SEQ ID NO:4) contains 213 amino acid residues, which is calculated to have a molecular weight of 25,193 and a pI of 10.1.

It should be noted that members of the genus Mycoplasma are characterized by an alternative codon usage wherein the UGA universal stop codon is read as tryptophan. A. Muto et al., *Transcription and Translation, in Mycoplasmas*: Molecular Biology and Pathogenesis 331–47 (J. Maniloff et al. eds., 1992). Thus mycoplasma genes containing UGA tryptophan codons express truncated translation products or are not expressed at all in expression hosts that use UGA as a stop codon, such as *E. coli* and yeast. The sequence of the MAM gene (SEQ ID NO:3) reveals three UGA codons, at amino acid positions 132, 177, and 178 of the mature protein (SEQ ID NO:4). Therefore, to achieve expression of MAM in *E. coli*, these UGA tryptophan codons were changed to UGG tryptophan codons by site-directed mutagenesis using polymerase chain reaction (PCR). The resulting recombinant MAM gene should be useful for expression of MAM in any expression system in which UGA codons are read as stop codons.

Site-directed mutagenesis was performed as follows. A 1.4 kb XbaI fragment containing the mam gene was subcloned into plasmid pTZ18R (Pharmacia) to give plasmid zX1.4B. The following mutagenic primers were used in a PCR reaction using zX1.4B as a template to change the UGA codons at amino acid positions 177 and 178 to UGG codons:

GAAGAGATCT AAACCACCAG AGCTC (SEQ ID NO:5)

GATAAAGCTG TCAAACTAAC T (SEQ ID NO:6).

PCR was carried out according to methods well known in the art: U.S. Pat. Nos. 4,683,195; 4,683,202; 4,800,159; 4,965,188; PCR Technology: Principles and Applications for DNA Amplification (H. Erlich ed., Stockton Press, New York, 1989); PCR Protocols: A guide to Methods and Applications (Innis et al. eds, Academic Press, San Diego, Calif., 1990). This reaction also introduced a conservative nucleotide change wherein the CTT leucine codon at amino acid position 176 was changed to a CTC leucine codon, which also introduced a unique SacI restriction enzyme site into the mam gene. Following digestion of plasmid zX1.4B and the PCR product with restriction enzyme BglII, these two digested DNAs were ligated together to yield plasmid WWII-E. These nucleotide changes were confirmed by nucleotide sequencing.

The UGA to UGG change at amino acid position 132 was achieved with overlap PCR, S. N. Ho et al., Site-Directed Mutagenesis by Overlap Extension Using the Polymerase Chain Reaction, 77 Gene 51 (1989), hereby incorporated by reference. Briefly, a pair of complementary mutagenic primers was designed and synthesized:

GTTTGACTGC TTTATCCCAT AACTCTTG 28 (SEQ ID NO:7)

CAAGAGTTAT GGGATAAAGC TGTCAA
AC 28 (SEQ ID NO:8).

Another pair of primers was also designed and synthesized for use in the mutagenesis reaction as follows:

TCAGAATTCA TGAAACTTAG AGTTG
AAATC TT (SEQ ID NO:9)

AAAAAGCTTG CAAGGAATTT ATTTA
AAATC CCCCC (SEQ ID NO:10).

One PCR reaction was carried out using the SEQ ID NO:9 and SEQ ID NO:7 primers and plasmid WWII-E as the template, which yielded a PCR product corresponding to the 5' end of the mam gene through the mutation at amino acid position 132 with an EcoRI restriction site on the 5' end of the fragment. Another PCR reaction was also carried out using the SEQ ID NO:8 and SEQ ID NO:10 primers and plasmid WWII-E as the template, which yielded a PCR product from the mutation at position 132 through the 3' end of the man gene including a HindIII site at the 3' of the fragment. These two PCR products were then used as templates for the final PCR reaction using the SEQ ID NO:9 and SEQ ID NO:10 primers. The resulting PCR product (SEQ ID NO:11) encodes a recombinant MAM protein (rMAM1) having the amino acid sequence given in SEQ ID NO:4, as confirmed by sequencing.

Figure 2:
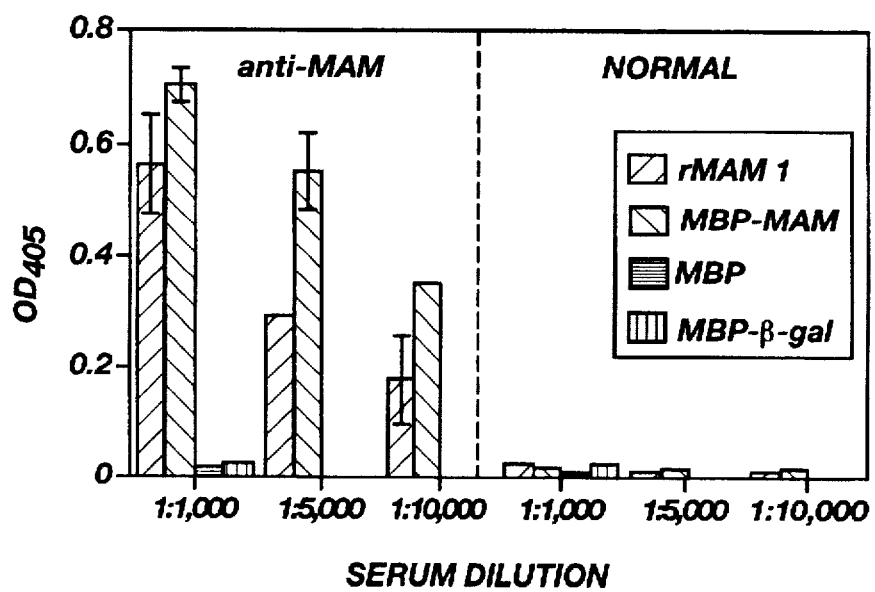
FIG. 2 shows a graphic representation of immunoreactivity of a recombinant MAM (rMAM; SEQ ID NO:13) and MBP-MAM fusion protein (MBP-rMAM) to murine antibodies against native MAM as compared to MBP, MBP-β-gal, and normal serum controls.

To confirm that the mutated gene of SEQ ID NO:11 encodes a recombinant MAM protein, the SEQ ID NO:11 PCR product was digested with EcoRI and HindIII and directionally cloned into the similarly digested pMAL-c2 protein fusion expression vector (New England Biolabs, Beverly, Me.). The pMAL vectors are described in C. Guan et al., 67 Gene 21 (1987); C. V. Maina et al., 74 Gene 365 (1988); P. Riggs, in *Current Protocols in Molecular Biology* (F. M. Ausubel et al. eds., 1990). Briefly, pMAL-c2 contains the malE gene, which encodes the approximately 45 kDa maltose-binding protein (MBP). A polylinker sequence is positioned downstream of the male gene such that cloning into the polylinker sequence results in expression of a MBP-fusion protein. The vector contains the strong $P_{tac}$ promoter and the translation initiation signals of MBP to express large amounts of fusion protein, up to about 30% of cellular protein. The pMAL-c2 vector lacks the male signal sequence, therefore the fusion protein accumulates in the cytoplasm. Between the malE sequence and the polylinker there is a spacer sequence coding for 10 asparagine residues, which insulates MBP from the protein of interest and increases the chances that the fusion protein will bind tightly to an amylose resin having affinity for MBP. The pMAL-c2 vector also includes a sequence coding for the recognition site (Ile-Glu-Gly-Arg; SEQ ID NO:12) of the protease, factor Xa. The presence of this factor Xa recognition site allows the protein of interest to be cleaved from MBP after purification. K. Nagai & H. C. Thogersen, 153 Meth. Enzymol. 461 (1987).

The resulting MBP-MAM expression vector was transformed into *E. coli*, grown in culture, and then induced by addition of isopropylthio-β-D-galactoside (IPTG), a gratuitous inducer of the lac operon, according to procedures well known in the art, e.g. U.S. Pat. No. 5,395,753. Purification of a recombinant MAM fusion protein was according to the method of Kellerman and Ferenci, 90 *Meth. Enzymol.* 459 (1982). Briefly, a crude cell extract was passed through an amylose resin column such that the MBP-MAM fusion protein was bound to the amylose resin and all other proteins were washed out. The MBP-MAM fusion protein was then eluted in purified form with maltose. The purified MBP-MAM fusion protein was then digested with the specific protease, factor Xa, to cleave MBP from the recombinant MAM protein. Recombinant MAM was purified from MBP by passing the mixture of proteins over an amylose resin column such that the MBP bound to the resin and recombinant MAM was in the flow through solution.

It should be recognized that the recombinant cleaved MAM produced by this procedure (SEQ ID NO:13) contains four extra amino acid residues (residues 1–4 of SEQ ID NO:13) covalently coupled to the N-terminus of mature MAM protein. Therefore, the MBP-MAM fusion protein contains the following elements in the order stated: MBP- (spacer of 10 asparagine residues)-(factor Xa recognition site)-(rMAM1; SEQ ID NO:13).

EXAMPLE 1

$V_\beta$ usage by MAM and other control superantigens was measured by IL-2 production by specific $V_\beta$-TCR bearing T hybridomas in the presence of gamma-irradiated 2PK-3 AC (both at $10^5$ cells/ml) according to the method of B. C. Cole et al., *Immunomodulation in vivo by the Mycoplasma arthritidis Superantigen*, MAM, 17 *Clin. Infect.* Dis. S163 (1993), hereby incorporated by reference. *Staphylococcus enterotoxins* A and B (SEA and SEB) were obtained from Toxin Technology (Sarasota, Fla.) and concanavalin A (Con A) from Sigma Chemical Co. (St. Louis, Mo.). The results of this $V_\beta$ TCR usage by native MAM and recombinant MAM are shown in Table 1.

TABLE 1

| | IL-2 (U/ml) produced by T hybridomas + APCs | | | | |
|---|---|---|---|---|---|
| Inducer[a] | $V_\beta1$ | $V_\beta3$ | $V_\beta8.2$ | $V_\beta11$ | $V_\beta6$ |
| None | 0 | 0 | 0 | 0 | 0 |
| MAM | 0 | 0 | 232 | 0 | 640 |
| rMAM | 0 | 0 | 428 | 0 | 612 |
| SEA | 691 | 1883 | 0 | 1181 | NT[b] |
| SEB | 0 | 1832 | 608 | 0 | 0 |
| Con A | 310 | 22240 | 315 | 2560 | 539 |

[a]Native MAM (SEQ ID NO:4) and recombinant MAM (rMAM; SEQ ID NO:13) were tested at approximately ≦ 50 ng/ml; SEA and SEB at 5 μg/ml; and Con A at 15 μg/ml.
[b]NT = not tested.

These results show that rMAM1 (SEQ ID NO:13) and native MAM exhibited an identical $V_\beta$ usage that was distinct from that of other superantigens. Therefore, a recombinant MAM containing 4 additional amino acid residues attached to the N-terminus of MAM is biologically active and appears to have the same biological properties as native MAM with respect to $V_\beta$ usage.

EXAMPLE 2

The MBP-MAM fusion protein was tested for $V_\beta$ usage according to the procedure of Example 1. The results showed that the MBP-MAM fusion protein exhibited an identical $V_\beta$ usage as native MAM, which was distinct from that of other superantigens. Therefore, the MBP-MAM fusion protein is biologically active.

EXAMPLE 3

Native MAM, rMAM1 (SEQ ID NO:13), and the MBP-MAM fusion protein were tested for their ability to stimulate lymphocyte proliferation according to the standard procedure using incorporation of tritiated thymidine into replicated DNA, B. Cole, 2 Methods in Mycoplasmology 389 (1983), hereby incorporated by reference. A fusion protein comprising MBP and β-galactosidase was used as a negative control, and Con A was used as a positive control. FIG. 1 shows the results of this experiment wherein native MAM, rMAM1 (SEQ ID NO:13), and the MBP-MAM fusion protein were substantially identical in their ability to stimulate lymphocyte proliferation.

EXAMPLE 4

Murine antibodies to native MAM were prepared according to methods well known in the art, e.g. E. Harlow & D. Lane, Antibodies: A Laboratory Manual (Cold Spring Harbor Press, Cold Spring Harbor, N.Y., 1988). These anti-MAM antibodies were tested for the ability to recognize rMAM1 (SEQ ID NO:13) and the MBP-MAM fusion protein by ELISA. MBP and an MBP-β-galactosidase fusion protein were used as controls, and a control experiment with normal serum was also carried out. The results of this test, FIG. 2, show that rMAM1 (SEQ ID NO:13) and the MBP-MAM fusion protein were substantially identical with respect to immune recognition by anti-MAM antibodies.

EXAMPLE 5

The anti-MAM antibodies of Example 4 were used to test the ability of such antibodies to block lymphocyte proliferation. Anti-MAM antibodies were incubated with rMAM1 (SEQ ID NO:13) and the MBP-MAM fusion protein prior to incubating these versions of MAM protein with genetically responsive murine splenocytes, according to the standard procedure using incorporation of tritiated thymidine into replicated DNA. B. Cole, 2 Methods in Mycoplasmology 389 (1983). The results of this test showed that anti-MAM antibodies blocked the ability of native MAM, recombinant MAM, and the MBP-MAM fusion protein to stimulate lymphocyte proliferation.

EXAMPLE 6

Rabbit antibodies to the MBP-MAM fusion protein were prepared according to methods well known in the art, e.g. E. Harlow & D. Lane, Antibodies: A Laboratory Manual (Cold Spring Harbor Press, Cold Spring Harbor, N.Y., 1988). These MBP-MAM antibodies were tested for the ability to recognize native MAM, rMAM1 (SEQ ID NO:13), and the MBP-MAM fusion protein by ELISA. The results of this test showed that native MAM, rMAM1, and the MBP-MAM fusion protein were substantially identical with respect to immune recognition by anti-recombinant-MAM antibodies.

EXAMPLE 7

Figure 3:
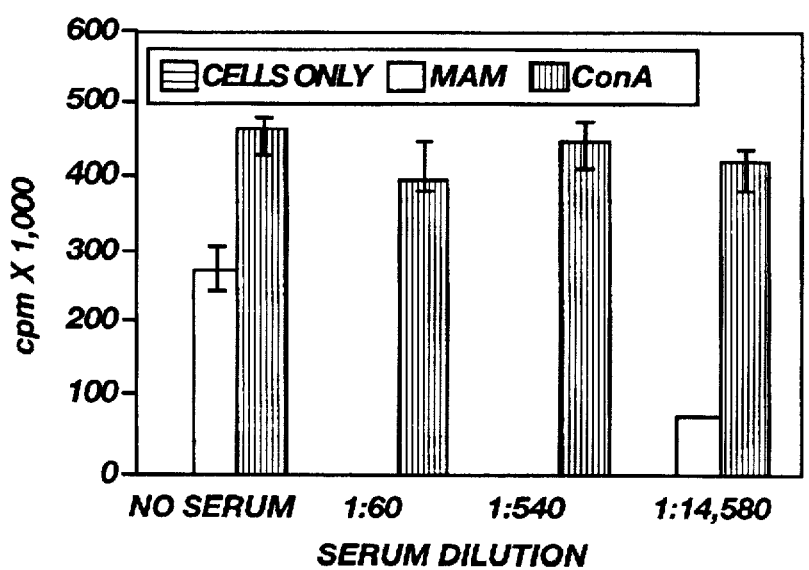
FIG. 3 shows a graphic representation of blocking of lymphocyte proliferation induced by native MAM by rabbit antiserum against the MBP-MAM fusion protein as compared to uninduced and Con A controls.

The anti-MBP-MAM antibodies of Example 6 were used to test the ability of such antibodies to block lymphocyte proliferation. Anti-MBP-MAM antibodies were incubated with native MAM protein prior to incubation with genetically responsive murine splenocytes, according to the standard procedure using incorporation of tritiated thymidine into replicated DNA. B. Cole, 2 Methods in Mycoplasmology 389 (1983). The results of this test, FIG. 3, showed that anti-MBP-MAM antibodies blocked the ability of native MAM protein to stimulate lymphocyte proliferation.

EXAMPLE 8

The abilities of native MAM, rMAM1 (SEQ ID NO:13), and the MBP-MAM fusion protein to associate class II major histocompatibility complex (MHC) molecules was tested by determining the level of tritiated thymidine uptake into lymphocytes from mouse strains that possess or lack the I-$E_\alpha$ chain of the murine MHC. The results of this test are shown in Table 2.

TABLE 2

| | Uptake of $^3$H-TdR by Mouse Lymphocytes[a] | | | | | |
|---|---|---|---|---|---|---|
| | BALB/c ($E_\alpha^+$) | B10.RIII ($E_\alpha^+$) | C3H ($E_\alpha^+$) | C3H.SW ($E_\alpha^-$) | C57BL/10 ($E_\alpha^-$) | SWR ($E_\alpha^-$) |
| nMAM[b] | 108.2 | 50.9 | 116.8 | 1.3 | 0.1 | 0 |
| MBP-MAM | 80.7 | 52.0 | 170.2 | 0 | 0.5 | 0.1 |
| rMAM1[c] | 114.9 | 96.2 | 108.2 | 0 | 0.2 | 1.0 |

[a]Values expressed are counts per minute × $10^{-3}$ in MAM-treated lymphocytes minus counts in untreated lymphocytes.
[b]Native MAM
[c](SEQ ID NO:13)

The results of this experiment show that MHC recognition is substantially identical for native MAM, rMAM1 (SEQ ID NO:13), and the MBP-MAM fusion protein, i.e. all of the $E_\alpha^+$ mice are positive and all of the $E_\alpha^-$ mice are negative.

EXAMPLE 9

In this example, the stability of native MAM, rMAM1 (SEQ ID NO:13), and the MBP-MAM fusion protein were compared. Native MAM is known in the art to be highly unstable because of heat and acid (pH<7.0) lability and great affinity for binding to surfaces and large molecules, such as proteins and nucleic acids. The protein rMAM1 (SEQ ID NO:13) was observed to have stability properties substantially similar to native MAM, i.e. rMAM1 is very sticky and as a result give poor chromatographic separation. On the other hand, the MBP-MAM fusion protein was observed to retain biological activity after storage for greater than 1 year at 4° C. in a plastic tube.

EXAMPLE 10

In this example, a recombinant MAM gene was expressed in *E. coli* using the "QIAexpress" system from Qiagen Inc. (Chatsworth, Calif.). The "QIAexpress" system is designed to attach a polyhistidine tag to the expressed protein of interest to facilitate subsequent purification. E. Hochuli, Purification of Recombinant Proteins with Metal Chelate Adsorbent, in 12 *Genetic Engineering, Principles and Methods* 87–98 (J.K. Setlow ed., 1990). The polyhistidine tag, consisting of six consecutive histidine residues, permits a one-step purification of the protein by metal ($Ni^{2+}$) affinity chromatography. R. Janknecht et al., Rapid and Efficient Purification of Native Histidine-tagged Protein Expressed by Recombinant Vaccinia Virus, 88 Pro. Nat'l Acad. Sci. USA 8972 (1991).

Expression in this system was achieved by first constructing a recombinant MAM gene derivative with an in-frame motif coding for a C-terminal polyhistidine tag using PCR. The following primers were designed and synthesized:

ACAGAATTCA TTAAAGAGGA GAAATTAACC
ATGAAACTTA GAGTTGAAAA TCCTAA
AAAA GC (SEQ ID NO:14)

GTAAGCTTAG TGATGGTGAT GGTGATGATC
TTCAAAAACA GCTTTTGC (SEQ ID NO:15)

A PCR reaction was performed using SEQ ID NO:14 and SEQ ID NO:15 primers and the MBP-MAM expression vector described above as template. The resulting product comprises a DNA fragment with a 5'-proximal EcoRI site followed by a ribosomal binding site, MAM gene (SEQ ID NO:11), coding sequence for 6 histidine residues, and a 3'-proximal HindIII restriction site. This fragment was digested with both EcoRI and HindIII and ligated to a similarly digested plasmid. pQE60 (Qiagen), to generate plasmid pKK22. Induction with IPTG of an appropriate *E. coli* strain transformed with pKK22 results in expression of a recombinant MAM protein (SEQ ID NO:16) with 6 histidine residues appended to the C-terminus, i.e. a C-terminal histidine tag.

EXAMPLE 11

The procedure of Example 10 was followed except that the PCR reaction was carried out with the SEQ ID NO:17 and SEQ ID NO:18 primers and the MBP-MAM expression plasmid as the template. These primers are as follows:

CACACCATGG GACATCACCA TCACCATCAC
ATGAAACTTA GAGTTGAAAA TCCTAA
AAA GC                              (SEQ ID NO:17)

AGCTAAGCTT TAATCTTCAA AAACAGCT
TT TCG                              (SEQ ID NO:18)

The product of this reaction is similar to the product of the PCR reaction of Example 10 except that the fragment contains a 5'-proximal NcoI restriction site instead of an EcoRI site and the polyhistidine tag is encoded at the N-terminus of the MAM gene. This fragment was digested with both NcoI and HindIII and was ligated into similarly digested plasmid pQE60 to generate plasmid pKK23. Induction with IPTG of an appropriate *E. coli* strain transformed with pKK23 results in expression of a recombinant MAM protein (SEQ ID NO:19) with 6 histidine residues appended to the N-terminus, i.e. a N-terminal histidine tag.

EXAMPLE 12

A PCR reaction was carried out according to the procedure of Example 11 except that SEQ ID NO:20 primer was used instead of SEQ ID NO:18 primer:

AAAAAGCTTG CAAGGAATTT ATTTAA
AATC CCCCC                          (SEQ ID NO:20)

The product of this reaction is similar to the product of the PCR reaction of Example 11 except that the SEQ ID NO:20 binds to the MBP-MAM template downstream of the translation termination signal. This fragment was digested with both NcoI and HindIII and was ligated into similarly digested plasmid pQE60 to generate plasmid pKK24. Induction with IPTG of an appropriate *E. coli* strain transformed with pKK24 results in expression of a recombinant MAM protein (SEQ ID NO:19) with 6 histidine residues appended to the N-terminus, i.e. a N-terminal histidine tag.

EXAMPLE 13

The protein expressed by the procedure of Example 10 was purified by sonicating the induced cells and then clarifying the sonicated cells by centrifugation to remove cell debris. The clarified cell extract was loaded on a $Ni^{2+}$ affinity column, washed to remove unbound material, and the purified protein was eluted with a step gradient. J. Janknecht et al., supra. SDS-PAGE analysis of the eluted fractions showed a protein of about 26 kDa.

The recombinant MAM protein (SEQ ID NO:16) purified by this procedure was tested for ability to stimulate lymphocyte proliferation according to the method of Example 3. The SEQ ID NO:16 protein exhibited an ability to stimulate lymphocyte proliferation that was substantially equivalent to that of native MAM, recombinant MAM (SEQ ID NO:13), and the MBP-MAM fusion protein.

EXAMPLE 14

The protein expressed by the procedures of Examples 11 and 12 was purified by the method of Example 13. The recombinant MAM protein (SEQ ID NO:19) purified by this procedure comigrated in polyacrylamide gel electrophoresis with rMAM prepared as described in Example 10.

EXAMPLE 15

Eleven overlapping peptides that together span the entire length of the MAM protein were synthesized and tested for ability to compete with MAM-induced lymphocyte proliferation. Two of these peptides, $MAM_{15-31}$ and $MAM_{71-95}$, inhibited MAM-induced lymphocyte proliferation. One of these, $MAM_{15-31}$, was described in U.S. patent application Ser. No. 08/165,038. To determine the amino acid residues essential for MAM to induce lymphocyte proliferation, site-directed mutagenesis of a recombinant MAM (SEQ ID NO:13) was carried out by overlapping PCR, Ho et al., supra. Three mutants with changes in the region of the $MAM_{15-31}$ peptide were constructed and tested for mitogenic activity by the method described above in Example 3. In these mutant proteins, alanine residues were substituted for the amino acid residues normally occurring at selected loci, as follows. In mutant protein KK21 (SEQ ID NO:21), alanine residues were substituted for residues 15–20 of native MAM (residues 19–24 of SEQ ID NO:13). In mutant protein KK19, alanine residues were substituted for residues 21–26 of native MAM (residues 25–30 of SEQ ID NO:13). In mutant protein KK20, alanine residues were substituted for residues 26–31 of native MAM (residues 30–35 of SEQ ID NO:13). The recombinant MAM protein KK21 (SEQ ID NO:21) exhibited mitogenic activity substantially equivalent to that of the recombinant MAM protein of SEQ ID NO:13.

EXAMPLE 16

The region encompassed by $MAM_{71-95}$ was found to contain the lectin-legume motif β, which is present in all plant lectins including Con A. N. Sharon & H. Liss, Legume lectins, a large family of homologous proteins, 4 FASEB 198–3208 (1990). This motif (SEQ ID NO:30) is found in amino acid residues 83–89 of MAM (SEQ ID NO:4) and residues 87–93 of rMAM1 (SEQ ID NO:13). To determine the amino acid residues essential for MAM to induce lymphocyte proliferation, site-directed mutagenesis of rMAM1 (SEQ ID NO:13) was carried out and the resulting proteins were tested for mitogenic activity according to the method of Example 15.

Replacement of residues 83–89 of MAM (residues 87–of SEQ ID NO:13) with alanine residues (recombinant protein KK12; SEQ ID NO:24) or the Con A version (SEQ ID NO:31) of the motif (recombinant protein KK13; SEQ ID NO:25) resulted in complete loss of activity. Moreover, insertion of an extended Con A version (SEQ ID NO:32) of the motif (recombinant protein KK14; SEQ ID NO: 26) also failed to exhibit activity. Changing the alanine residues 87–of protein KK12 to those of the original recombinant MAM protein (SEQ ID NO:13) restored activity. Amino acid residue substitutions just outside the motif at residue 82 of MAM (residue 86 of SEQ ID NO:13; recombinant MAM protein KK17; SEQ ID NO:27) or residue 90 of MAM (residue 94 of SEQ ID NO:13; recombinant MAM protein KK18; SEQ ID NO:28) or of the conserved aspartic acid residue of the lectin legume motif-β at position 88 of MAM (residue 92 of SEQ ID NO:13; recombinant MAM protein KK11; SEQ ID NO:29) resulted in recombinant MAM proteins with lymphoproliferative ability.

EXAMPLE 17

As disclosed in Ser. No. 08/165,038, superantigens may be involved in the triggering or induction of flares in human rheumatoid disease. Evidence of such exposure to superantigens would include the development of antibodies to superantigens in the sera of individuals with such a disease. Native MAM, recombinant MAM, or the MBP-MAM fusion protein can be used in a traditional ELISA assay, e.g. U.S. Pat. No. 5,395,753, to detect the presence of antibodies to MAM in various autoimmune conditions.

Figure 4:
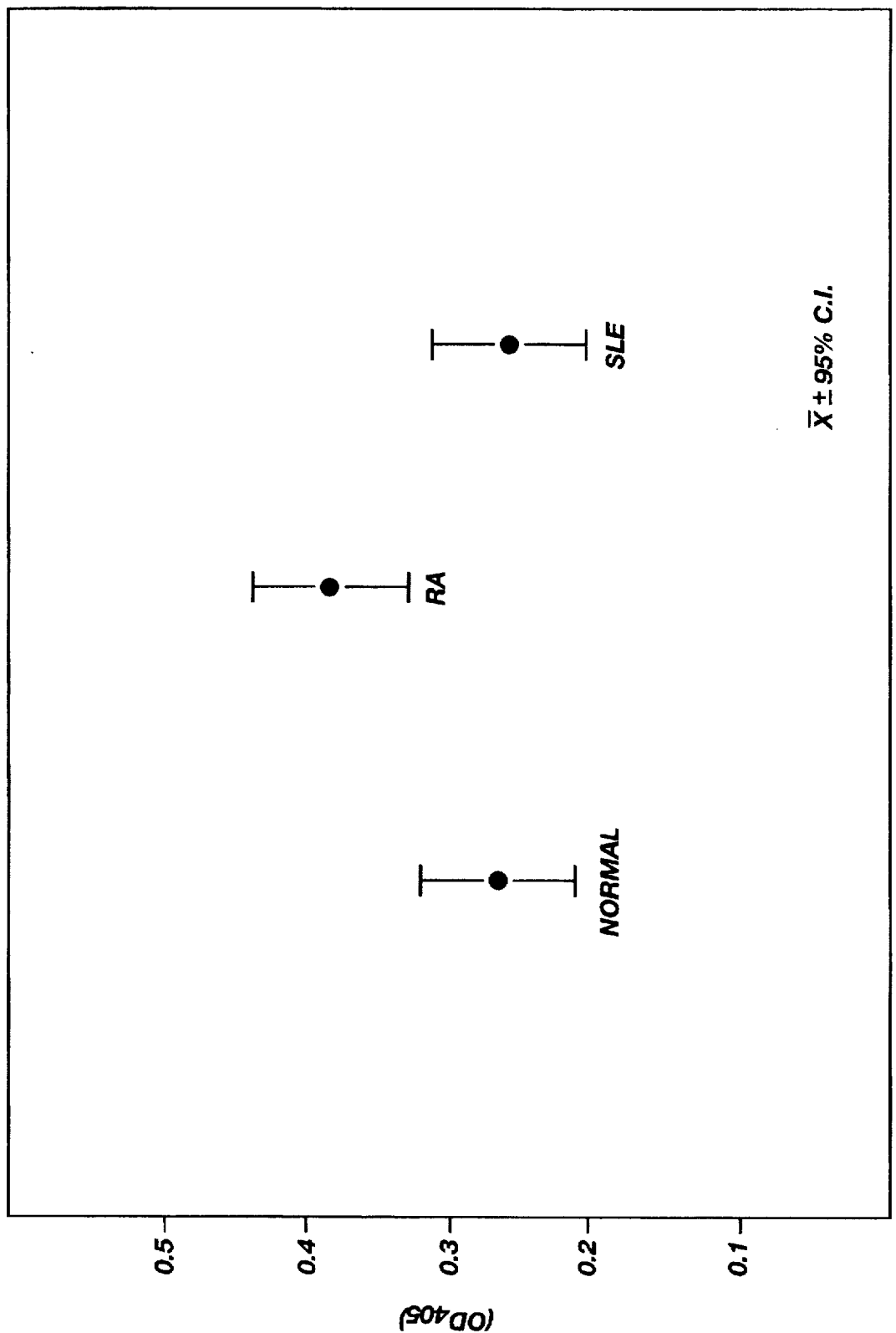
FIG. 4 shows a graphic representation of binding of antibodies in sera from rheumatoid arthritis (RA), systemic lupus erythematosus (SLE), and normal subjects to recombinant MAM by ELISA; 95% confidence intervals are shown.

FIG. 4 shows the results of such an ELISA assay wherein rMAM1 (SEQ ID NO:13) was bound to the wells of a microtiter plate and the presence of anti-MAM antibodies in the sera of 32 rheumatoid arthritis (RA), 24 normal, and 13 systemic lupus erythematosus subjects was assayed. The sera of RA patients showed significantly higher reactivity to MAM than did either the normal or SLE subjects, suggesting the presence of anti-MAM antibodies therein. The reactivities of normal sera and SLE sera were substantially equivalent for binding to MAM. These results suggest that native MAM, recombinant MAM proteins, and the MBP-MAM fusion protein can be used in a diagnostic test for RA. The test comprises binding a MAM protein to a solid support, such as a microtiter plate; exposing the sera to be tested to the support-bound MAM protein such that anti-MAM antibodies in the sera bind with the support-bound MAM protein; washing away unbound antibodies; and detecting the presence of the bound antibodies, such as with a labeled anti-human antibody. The amount of label bound to the microtiter plate is a measure of the amount of anti-MAM antibody in the sera.

EXAMPLE 18

The MAM superantigen has been shown to trigger, exacerbate or enhance arthritis in mice that are immunized with articular type II collagen. This is caused by expanding collagen-reactive T cells bearing $V_\beta 6$, $V_\beta 7$, and $V_\beta 8$ TCRs.

Since antibodies to MAM neutralize the ability of MAM to stimulate T cell activation, vaccination of individuals against MAM would protect against development of murine arthritis triggered by MAM in animals possessing collagen-reactive T cells. Because the injection of active, native MAM into naive mice is toxic and drastically modifies the immune system, native MAM is not a sound choice for an immunogen.

As disclosed above, a recombinant MAM protein that has been modified by site-directed mutagenesis to substitute alanine residues at certain active regions of the molecule no longer activates murine lymphocytes. Furthermore, it has also been determined that inactive recombinant MAM proteins are recognized by antibodies against native MAM. Therefore, a non-toxic modified MAM protein could be used as immunogen to produce antibodies that will protect against the ability of native MAM to activate lymphocytes and hence trigger autoimmune arthritis. Immunization procedures using proteins are well known in the art, e.g. G. Edsall, Specific prophylaxis of tetanus, 171 *J. Am. Med. Assoc.* 471 (1959).

Superantigens have been postulated as playing a role in human autoimmune arthritis and, as disclosed, patients with rheumatoid arthritis exhibit enhanced antibody response to MAM, suggesting prior exposure to a MAM-like superantigen. Also, the disease-causing active lymphocytes in the joints of human rheumatoid arthritis patients show an increase in T cells bearing those human $V_{\beta}$ TCRs that are used by MAM. M. D. Howell et al., 88 Proc. Nat'l Acad. Sci USA 10921 (1991); W. V. Williams, 12 DNA Cell. Biol. 425 (1993); Y. Li et al., 6 *J. Clin. Invest.* 2525 (1994); G. Zagon et al. 37 *Arthritis Rheum.* 1431 (1994).

Therefore, inactive MAM-like proteins can be used as immunogens to protect against the development or exacerbation of rheumatoid arthritis of humans.

We claim:

1. A recombinant MAM protein that exhibits superantigen activity comprising an amino acid sequence identified as SEQ ID NO:19.

2. A recombinant MAM protein that exhibits superantigen activity comprising an amino acid sequence comprising SEQ ID NO:4 and at least one additional amino acid residue at a C-terminus thereof.

3. The recombinant MAM protein of claim 2 wherein the amino acid sequence is SEQ ID NO:16.

4. A recombinant MAM protein that exhibits superantigen activity having an amino acid sequence selected from the group consisting of SEQ ID NO:16, SEQ ID NO:19, SEQ ID NO:21, SEQ ID NO:27, SEQ ID NO:28, and SEQ ID NO:29.

5. The recombinant MAM protein of claim 4 wherein the amino acid sequence is SEQ ID NO:16.

6. The recombinant MAM protein of claim 4 wherein the amino acid sequence is SEQ ID NO:19.

7. The recombinant MAM protein of claim 4 wherein the amino acid sequence is SEQ ID NO:21.

8. The recombinant MAM protein of claim 4 wherein the amino acid sequence is SEQ ID NO:27.

9. The recombinant MAM protein of claim 4 wherein the amino acid sequence is SEQ ID NO:28 .

10. The recombinant MAM protein of claim 4 wherein the amino acid sequence is SEQ ID NO:29.

11. A recombinant MAM protein represented by the formula: MBP-S-X-rMAM, wherein MBP is the maltose binding protein, S is a spacer, X is a factor Xa protease recognition sequence, and rMAM is a polypeptide having an amino acid sequence selected from the group consisting of SEQ ID NO:21; SEQ ID NO:27, SEQ ID NO:28, and SEQ ID NO:29.

12. The recombinant MAM protein of claim 11 wherein the amino acid sequence of rMAM is SEQ ID NO:21.

13. The recombinant MAM protein of claim 11 wherein the amino acid sequence of rMAM is SEQ ID NO:27.

14. The recombinant MAM protein of claim 11 wherein the amino acid sequence of rMAM is SEQ ID NO:28.

15. The recombinant MAM protein of claim 11 wherein the amino acid sequence of rMAM is SEQ ID NO:29.

16. The recombinant MAM protein of claim 11 wherein X is SEQ ID NO:12.

17. The recombinant MAM protein of claim 16 wherein S comprises 10 asparagine residues.

* * * * *